(12) United States Patent
Valenzuela et al.

(10) Patent No.: US 7,056,658 B2
(45) Date of Patent: Jun. 6, 2006

(54) MULTIPLE EPITOPE FUSION PROTEIN

(75) Inventors: Pablo D. T. Valenzuela, Berkeley, CA (US); David Ying Chien, Alamo, CA (US)

(73) Assignee: Chiron Corporation, Emeryville, CA (US)

( * ) Notice: Subject to any disclaimer, the term of this patent is extended or adjusted under 35 U.S.C. 154(b) by 822 days.

(21) Appl. No.: 10/174,652

(22) Filed: Jun. 17, 2002

(65) Prior Publication Data

US 2003/0044774 A1    Mar. 6, 2003

Related U.S. Application Data

(63) Continuation of application No. 08/653,226, filed on May 24, 1996, now Pat. No. 6,514,731.

(51) Int. Cl.
*C12Q 1/70* (2006.01)
*G01N 33/53* (2006.01)
*A61K 39/29* (2006.01)

(52) U.S. Cl. .......................... 435/5; 435/7.1; 424/228.1
(58) Field of Classification Search .................... 435/5, 435/7.1; 424/228.1
See application file for complete search history.

(56) References Cited

U.S. PATENT DOCUMENTS

| | | | |
|---|---|---|---|
| 4,403,036 A | 9/1983 | Hartley et al. ............... | 435/317 |
| 4,977,079 A | 12/1990 | Nuzzolo et al. ................ | 435/7 |
| 5,061,619 A | 10/1991 | Wilson et al. ................. | 435/5 |
| 5,218,099 A | 6/1993 | Reyes et al. ............. | 536/23.72 |
| 5,223,400 A | 6/1993 | Ling et al. .................. | 435/7.93 |
| 5,229,491 A | 7/1993 | Habets et al. ................ | 530/326 |
| 5,350,671 A | 9/1994 | Houghton et al. .............. | 435/5 |
| 5,582,968 A | 12/1996 | Wang et al. .................... | 435/5 |
| 5,639,594 A | 6/1997 | Wang et al. .................... | 435/5 |

FOREIGN PATENT DOCUMENTS

| | | |
|---|---|---|
| GB | 2 294 047 | 4/1996 |
| JP | 8-24045 | 10/1997 |
| JP | 9-278794 | 10/1997 |
| WO | 92/08734 | 5/1992 |
| WO | 93/00365 | 1/1993 |
| WO | 93/08280 | 4/1993 |

(Continued)

OTHER PUBLICATIONS

Chien et al., "Use of Recombinant HCV Antigen in the Serodiagnosis of Hepatitis C Virus Infection: Significant Improvement in HCV Antibody Detection as Compared with the First Generation HCV C100-3 ELISA and the Synthetic Peptide EIA Test" *J. Gastroentrerology and Hepatology* 8:S33-S-39, 1993.

(Continued)

*Primary Examiner*—J. S. Parkin
(74) *Attorney, Agent, or Firm*—Roberta L. Robins; Marcella Lillis; Alisa A. Harbin

(57) ABSTRACT

Multiple epitope fusion proteins and immunoassays using the same are disclosed. The multiple epitope fusion proteins are encompassed by the general structural formula $(A)_x-(B)_y-C_2$ which represents a linear amino acid sequence, wherein B is an amino acid sequence of an epitope or cluster of epitopes and each B contains at least five and not more than 1,000 amino acids, y is an integer of 2 or more, A and C are each independently an amino acid sequence of an epitope or cluster of epitopes not adjacent to B in nature and x and z are each independently an integer of 0 or more wherein at least one of x and z is 1 or more.

28 Claims, 9 Drawing Sheets

MEFA-3 ANTIGEN

| hSOD-(1-154) | CORE | CORE | c33c | 5-1-1 type 1 | 5-1-1 type 3 | 5-1-1 type 2 | C-100 | C-100 | NS5 | NS5 |
|---|---|---|---|---|---|---|---|---|---|---|
| AMINO ACIDS | 10-53 | 10-53 | 1192-1457 | 1694-1735 | 1694-1735 | 1694-1735 | 1901-1940 | 1901-1940 | 2278-2310 | 2278-2310 |

MEFA-5 ANTIGEN

| hSOD-(1-154) | CORE | CORE | E1 | E2 | c33c | 5-1-1 type 1 | 5-1-1 type 3 | 5-1-1 type 2 | C-100 | NS5 | NS5 |
|---|---|---|---|---|---|---|---|---|---|---|---|
| AMINO ACIDS | 10-53 | 10-53 | 303-320 | 405-444 | 1192-1457 | 1689-1735 | 1689-1735 | 1689-1735 | 1901-1940 | 2278-2313 | 2278-2313 |

MEFA-6 ANTIGEN

| hSOD-(1-154) | E1 | E2 | c33c | 5-1-1 type 1 | 5-1-1 type 3 | 5-1-1 type 2 | C-100 | NS5 | NS5 | CORE | CORE |
|---|---|---|---|---|---|---|---|---|---|---|---|
| AMINO ACIDS | 303-320 | 405-444 | 1192-1457 | 1689-1735 | 1689-1735 | 1689-1735 | 1901-1940 | 2278-2313 | 2278-2313 | 10-53 | 10-53 |

FOREIGN PATENT DOCUMENTS

| WO | 94/01778 | 1/1994 |
| --- | --- | --- |
| WO | 94/18234 | 8/1994 |
| WO | 94/27153 | 11/1994 |
| WO | 95/03825 | 2/1995 |
| WO | 95/33053 | 12/1995 |
| WO | 96/04301 | 2/1996 |

OTHER PUBLICATIONS

Chien et al., "Diagnosis of Hepatitis C Virus (HCV) Infection Using an Immunodominant Chimeric Polyprotein to Capture Circulating Antibodies: Reevaluation of the Role of HCV in Liver Disease" *Proc. Natl. Acad. Sci.* (USA) 89:10011-10015, 1992.

Chien et al., "Distinct Subtypes of Hepatitis C Virus Defined by Antibodies Directed to the Putative Core, NS4, and NS5 Region Polypeptides" *Viral Hepatitis and Liver Disease* 320-324, 1994.

Ching et al.,"Interaction of Immune Sera with Synthetic Peptides Corresponding to the Structural Protein Region of Hepatitis C Virus" *Proc. Natl. Acad. Sci.* (USA) 89:3190-3194, 1992.

Sallberg et al., "Immunodominant Regions Within the Hepatitis C Virus Core and Putative Matrix Proteins" *J. Clin. Microbiol.* 30(8):1989-1994, 1992.

Simmonds et al., *J. Clin. Microbiol.* 31:1493-1503, 1993.

Van der Poel et al., "Confirmation of Hepatitis C Virus Infection by New Four-Antigen Recombinant Immunoblot Assay" *Lancet* 337:317-319, 1991.

Smythe et al., "Production of Linear Polymers of HIV gp120-binding Domains" *Protein Eng.* 7(2):145-147, Feb., 1994.

Chatterjee et al., "Fine Specificity of Immune Responses to Epitopic Sequences in Synthetic Peptides Containing B and T Epitopes From the Conserved Plasmodium Flaciparum Blood-Stage Antigens" *Vaccine* 13(15):1474-1481, 1995.

Van der Ploeg et al., "Immunological Properties of Multiple Repeats of a Linear Epitope of Herpes Simplex Virus Type 1 Glycoprotein D" *J. Immunol. Methods* 124:211-217, 1989.

Brown et al., "Improved Diagnosis of Chronic Hepatitis C Virus Infection by Detection of Antibody to Multiple Epitopes: Confirmation by Antibody to Syntheitic Oligopeptides" *J. Medical Virology* 38(3):167-171, Nov., 1992.

Pujol et al., "Characterization of the Antibody Reactivity to Synthetic Peptides from Different Parts of the Hepatitis C Virus Genome" *Viral Immunology* 9(2):89-96, 1996.

Chen et al., "The Structural Influence of Individual Residues Located within Peptide Antigen Depends Upon Their Sequence Context" *Molecular Immunology* 31(14):1069-1075, Oct., 1994.

Londono et al., "Secondary Structure and Immunogenicity of Hybrid Synthetic Peptides Derived from Two Plasmodium Falciparum Pre-Erythrocytic Antigens" *J. Immunology* 145(5):1557-1563, Sep., 1990.

Yagi et al., "An Epitope Chimeric Antigen for the Hepatitis C Virus Serological Screening Test" *Biol. Pharm. Bull.* 19(10):1254-1260, 1996.

Ebeling et al., *Lancet* 337:912-913, 1991.

Kotwal et al., "Detection of Acute Hepatitis C Virus Infection by ELISA Using a Synthetic Peptide Comprising a Structural Epitope" *Proc. Natl. Acad. Sci.* (USA) 89:4486-4489, 1992.

Kuo et al., "An Assay for Circulating Antibodies to a Major Etiologic Virus of Human Non-A, Non-B Hepatitis" *Science* 244:362-364, 1989.

Machida et al., "Two Distinct Subtypes of Hepatitis C Virus Defined by Antibodies Directed to the Putative Core Protein" *Hepatology* 16:886-891, 1992.

Nasoff et al., "Identification of an Immunodominant Epitope Within the Capsid Protein of Hepatitis C Virus" *Proc. Natl. Acad. Sci.* (USA) 88:5462-5466, 1991.

Choo et al., "Genetic Organization and Diversity of the Hepatitis C Virus" *Proc. Natl. Acad. Sci.* (USA) 88:2451-2455, 1991.

Choo et al., "Isolation of a cDNA Clone Derived from a Blood-Borne Non-A, Non-B Viral Heaptitis Genome" *Science* 244:359-362, 1989.

MEFA-3 ANTIGEN

| hSOD-(1-154) | CORE | CORE | c33c | 5-1-1 type 1 | 5-1-1 type 3 | 5-1-1 type 2 | C-100 | C-100 | NS5 | NS5 |
|---|---|---|---|---|---|---|---|---|---|---|
| AMINO ACIDS | 10 - 53 | 10 - 53 | 1192 - 1457 | 1694 - 1735 | 1694 - 1735 | 1694 - 1735 | 1901 - 1940 | 1901 - 1940 | 2278 - 2310 | 2278 - 2310 |

MEFA-5 ANTIGEN

| hSOD-(1-154) | CORE | CORE | E1 | E2 | c33c | 5-1-1 type 1 | 5-1-1 type 3 | 5-1-1 type 2 | C-100 | NS5 | NS5 |
|---|---|---|---|---|---|---|---|---|---|---|---|
| AMINO ACIDS | 10 - 53 | 10 - 53 | 303 - 320 | 405 - 444 | 1192 - 1457 | 1689 - 1735 | 1689 - 1735 | 1689 - 1735 | 1901 - 1940 | 2278 - 2313 | 2278 - 2313 |

MEFA-6 ANTIGEN

| hSOD-(1-154) | E1 | E2 | c33c | 5-1-1 type 1 | 5-1-1 type 3 | 5-1-1 type 2 | C-100 | NS5 | NS5 | CORE | CORE |
|---|---|---|---|---|---|---|---|---|---|---|---|
| AMINO ACIDS | 303 - 320 | 405 - 444 | 1192 - 1457 | 1689 - 1735 | 1689 - 1735 | 1689 - 1735 | 1901 - 1940 | 2278 - 2313 | 2278 - 2313 | 10 - 53 | 10 - 53 |

FIG. 1

HCV Antibody Detection Correlation Study
MEFA (CLIA) vs. Commercial ELISA

Clinical Specimens N=666
* Sample confirmed by Second Generation RIBA is non-reactive Clinical Specimens N=266
* Sample confirmed by Second Generation RIBA is non-reactive

MULTIPLE EPITOPE FUSION PROTEIN

This applications is a continuation of U.S. patent application Ser. No. 08/653,226, filed May 24, 1996, now U.S. Pat. No. 6,514,731, from which application priority is claimed pursuant to 35 U.S.C. § 120 and which application is incorporated herein by reference in its entirety.

FIELD OF THE INVENTION

This invention relates generally to the fields of protein synthesis and immunoassays and specifically relates to methods of synthesizing long chains of amino acids that contain multiple copies of epitopes for viruses such as HCV, and to assay devices that utilize multiple epitopes to detect the presence of antibodies.

BACKGROUND OF THE INVENTION

In general, immunoassays are produced by first determining epitopes that are specifically associated with a virus and then determining which of the epitopes is preferred for the assay being developed. When the immunodominant epitopes are isolated, their sequences are determined, and genetic material for producing the immunodominant epitopes is produced. Methods of producing proteins by either chemical or biological means are known, as are assays used to detect the presence of antibodies to particular epitopes.

In producing immunoassays the overall object is to obtain an immunoassay which is both highly sensitive and highly selective. More specifically, the immunoassay must be designed such that it can detect even very low levels of the material it is designed to detect, i.e., it is highly sensitive. An assay having a high degree of sensitivity ensures that a sample, which has been tested, is not contaminated with the material the assay is designed to detect. For example, a highly sensitive assay that detects even the slightest presence of antibodies for a given virus is desirable in that it makes it possible to detect and thus discard samples that contain any amount of the antibody indicating that the samples contain the virus.

Although a high degree of sensitivity is desirable in an assay, it is not desirable if the assay is falsely indicating the presence of the material, i.e. the assay is providing a false positive result. Such false positive results can occur when the analyte has a high degree of similarity with another material present in the sample. The ability on an assay to differentiate between two similar but different materials relates to its selectivity.

An immunoassay with a high degree of selectivity will detect the presence of a material being assayed for even when that material is present in the sample in combination with other materials having a similar structure. Thus, a highly selective immunoassay will eliminate most false positive results. In general, as selectivity increases sensitivity decreases. This occurs, in part, due to the high degree of variability in viruses. Assays which are designed to be highly sensitive must take into account the high degree of variability between different viruses. As virus variability is accommodated to improve sensitivity, the selectivity decreases. Alternatively, as one produces an immunoassay that is more and more selective with respect to a particular virus, the likelihood of the assay becoming so selective as to have decreased sensitivity increases.

To a large extent the problem of providing for improved selectivity (less false positives) is dealt with by searching for and finding the most immunodominant epitopes. The problem of sensitivity (low concentration detection) is dealt with by providing immunodominant epitopes from a variety of different regions of the virus.

Current assays are designed to utilize relatively few peptides selected as "major epitopes" or highly immunodominant epitopes. The assay sensitivity is dependent on the number of major epitopes available on the solid support. If the availability of epitopes is limited by the number of peptides that can be coated on the solid phase, then that assay will have reduced sensitivity. These results can be demonstrated as poor assay dilution sensitivity and poor seroconversion sensitivities and/or false negative determinations (Chien, D. Y. et al. (1993) J. Gastroenterology and Hepatology 8:S33–39).

There is currently a need to improve the sensitivity and selectivity of assays for antibodies to pathogens in biological fluids and thereby improve diagnosis of pathogen infection resulting in improved screening of blood supplies.

SUMMARY OF THE INVENTION

Multiple copy fusion antigen (MEFA) immunoassays capable of detecting antibodies from multiple strains of a pathogen in a single assay are produced by (1) identifying nucleotide sequences that encode a plurality of different epitopes, including immunodominant components; (2) placing the nucleotide sequences into an expression cassette wherein at least two copies of a sequence coding for the same epitope region of an organism such as virus or corresponding regions of different strains of the virus is placed in a single cassette; (3) transforming a suitable host with one or more copies of the cassette in order to express sequences encoding epitopes, which sequences will include two or more copies of at least one epitope in a single chain antigen; (4) purifying the expressed multiple epitope antigen; and (5) adapting the purified multiple epitope antigen for an immunoassay, where adapting may include, but is not limited to, the following: coating the multiple epitope antigen on a surface of a substrate; covalently attaching a detectable marker to the multiple epitope antigen; and the like. The purified epitopes are encompassed by the general structural formula $(A)_x-(B)_y-(C)_z$ which represents a linear amino acid sequence. B is an amino acid sequence of at least five and not more than 1,000 amino acids of an antigenic determinant or cluster of antigenic determinants, and y is an integer of 2 or more. Each copy of B is an equivalent antigenic determinant (for example, each copy is an epitope from a different viral strain). A and C are each independently an amino acid sequence of an epitope or cluster of epitopes not immediately adjacent to B in nature; and, x and z are each independently an integer of 0 or more, wherein at least one of x and z is 1 or more. Preferably the y epitopes of B are equivalent antigenic determinants from different viral strains thereby increasing the variety of pathogens detectable by a single multiple epitope antigen. The selectivity is further improved by including immunodominant epitopes from the same region of two or more different strains of the same virus. More preferably, the equivalent antigenic determinants of B have different serotype specificity. Homology between the B epitopes is at least 30%, preferably at least 40%. The epitopes of the invention are more soluble, and are therefore more easily purified, than conventional epitopes. Further, the presence of repeating epitope sequences (1) decreases masking problems and (2) improves sensitivity in detecting antibodies by allowing a greater number of epitopes on a unit area of substrate. Sensitivity is further improved by placing the multiple copy epitopes of the invention on small spherical or irregularly shaped beads or microparticles thereby increasing the exposed surface area per given area of an assay device.

An object of the invention is to provide an amino acid sequence comprised of a plurality of epitopes wherein at least the antigenic determinant portion of at least one of the epitopes is repeated two or more times.

Another object of the invention is to provide a method of producing an immunoassay using multiple epitope fusion antigens.

A feature of the invention is that amino acid sequences that comprise multiple copies of a given epitope sequence have higher solubility as compared with amino acid sequences comprising only a single copy of any given epitope.

Another feature of the invention is that the nucleotide sequences encoding the epitopes are in a linear order that may be different from their linear order in the genome of the pathogen. Thus, the antigenic determinants of A, B, and C may be in a linear order different from the naturally occurring antigenic determinants of A, B and C. The linear order of the sequences of the invention is preferably arranged for optimum antigenicity of the expressed amino acid sequences comprising the multiple epitope fusion antigen.

An advantage of the invention is that the multi-epitope antigens of formula (I) can be more easily purified as compared with conventional epitopes.

Another advantage of the invention is that masking of an antigenic determinant can be reduced.

Another advantage of the invention is that the immunoassays utilizing the multiple epitope fusion antigens have improved sensitivity and selectivity.

Another advantage of the invention is that the multiple epitopes, particularly the repeated epitopes of B, provide an assay capable of detecting more than one pathogen or more than one strain of a single pathogen based on the type specificity of the epitopes.

Another feature of the invention is that the multiple epitope sequences of formula (I) can be designed to include a larger number and or longer sequences than are generally present on epitope sequences containing only a single copy of any given epitope.

Another advantage of the invention is that the design of the multi-epitope antigens as per formula (I) makes it possible to include a greater number of antigenic determinants on a unit area of surface of an immunoassay as compared to antigens containing only a single copy of any given epitope.

The invention also provides the advantage of improving the general specificity and sensitivity of serological tests when multiple epitopes are required and solid phase surface area is limiting. Additionally, immunoassay tests based on a single chimeric antigen will greatly simplify the manufacturing process, particularly for tests which require antigens labelled with detectable markers.

An embodiment of the invention further provides a rapid capture ligand immunoassay using multiple epitope fusion antigens that is simple and convenient to perform because it is a one step simultaneous assay. Detection is by the attachment of a detectable marker to a member of the antigen/antibody complex, preferably to the antigen. Attachment may be by covalent means or by subsequent binding of detectably labeled antibodies, such as a standard sandwich assay, or by enzyme reaction, the product of which reaction is detectable. The detectable marker may include, but is not limited to, a chromophore, an antibody, an antigen, an enzyme, an enzyme reactive compound whose cleavage product is detectable, rhodamine or rhodamine derivative, biotin, strepavidin, a fluorescent compound, a chemiluminescent compound, such as dimethyl acridinium ester (DMAE, Ciba Corning Diagnostics Corp.), derivatives and/or combinations of these markers.

In another embodiment of the invention, the capture ligand format assay contains a MEFA as an antigen, as well as, an additional detectable epitope added to the assay mixture. The additional detectable epitope may be a single epitope or multiple epitopes and may include, but is not limited to, the epitopes included in the MEFA, preferably epitopes from regions such as E1, E2 and c33c. According to this embodiment of the invention, the additional epitope is attached or attachable to a detectable marker as described above. Where the additional epitope has preferred characteristics such as conformation, glycosylation, and the like, the additional epitope is expressed as a recombinant polypeptide from a cell, which expression provides the epitope in a desired form. Preferably the epitope is obtainable from the cell using gentle isolation conditions that preserves the desired characteristics of the epitope. The cell may be any appropriate cell such as a mammalian cell, preferably a chinese hamster ovary (CHO), or a bacterial, yeast or insect cell from which the additional epitope can be isolated in the desired form.

These and other objects, advantages and features of the present invention will become apparent to those persons skilled in the art upon reading the details of the multiple copy epitopes, immunoassays, and methods for producing such as more fully set forth below, with reference being made to the accompanying general structural formula forming a part hereof wherein like symbols refer to like molecular moieties throughout.

BRIEF DESCRIPTION OF THE DRAWINGS

FIG. 1 is a schematic drawing showing the identification, amino acids encoded, and the arrangements of epitopes in MEFA-3, MEFA-5, and MEFA-6.

DETAILED DESCRIPTION OF EMBODIMENTS

Figure 2:
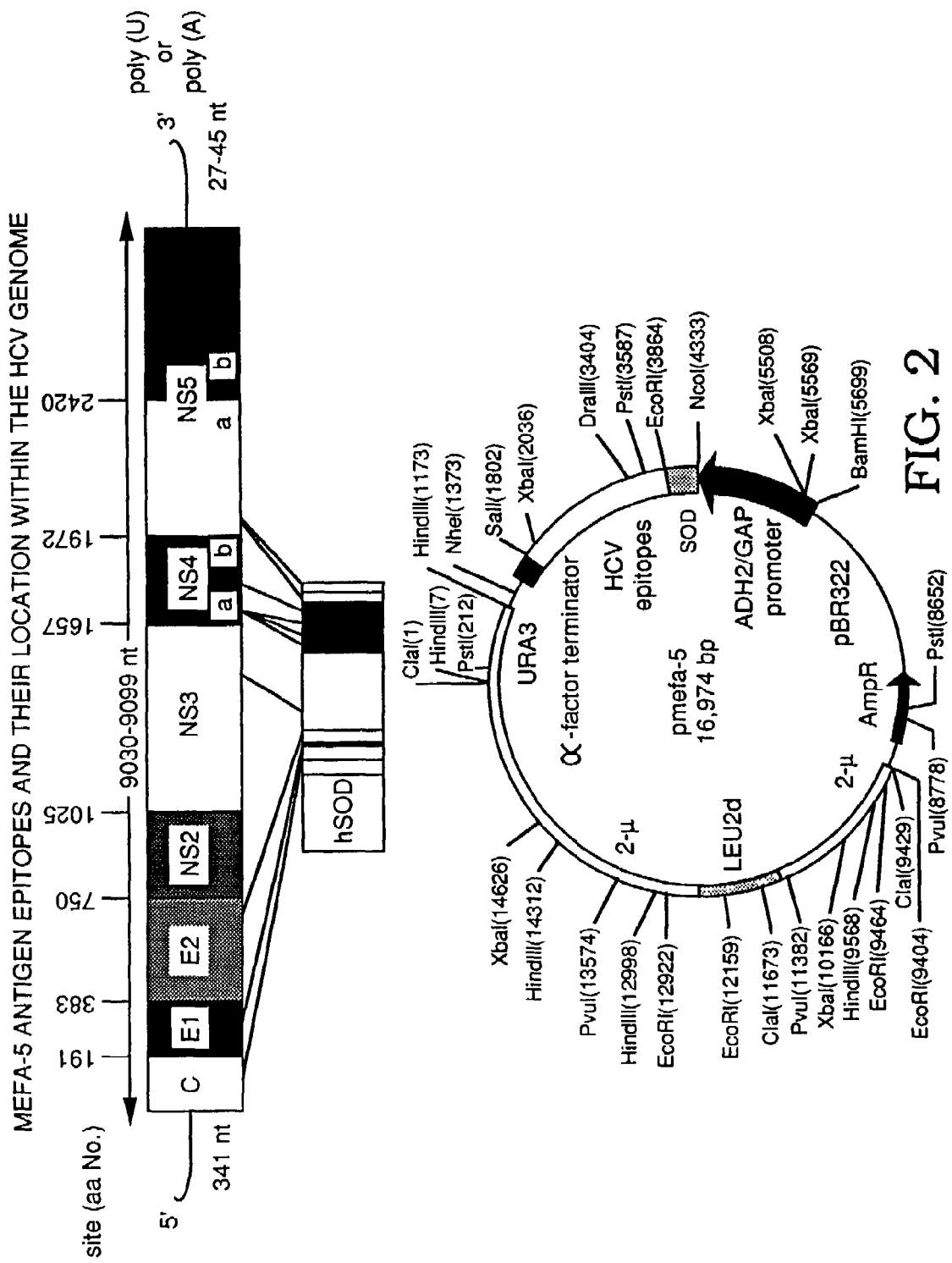
FIG. 2 is a schematic drawing showing the MEFA-5 antigen epitopes and their location within the HCV genome. A diagram of the expression vector for MEFA-5 is also provided.

Before the present multiple epitope fusion proteins, immunoassays and methods for producing and using such are described, it is to be understood that this invention is not limited to the particular amino acid sequences, immunoassays or methods of production as such may, of course, vary. It is also to be understood that the terminology used herein is for the purpose of describing particular embodiments only, and is not intended to be limiting since the scope of the present invention will be limited only by the appended claims.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of disclosing and describing the particular technology which the publication is cited in connection with.

Definitions

The term "multiple copy" shall mean that a sequence of amino acids which contains at least five and not more than 1,000 amino acids in a linear fashion is repeated two or more times within a linear molecule. The repeating sequence need not be directly connected to itself, is not repeated in nature in the same manner, and further may be present within a larger sequence which includes other amino acids not repeated or "copied." The sequence of at least five and not more than 1,000 amino acids comprises an epitope as defined below. For the purposes of this invention, a "copy" of an amino acid sequence may be either an exact sequence copy or a sequence which corresponds to the same epitope of a different viral strain, i.e. copies are either exact copies or sequences which are "equivalent antigenic determinants" as defined below.

The term "epitope" shall mean a sequence of at least five, and not more than 1,000 acids connected in a linear fashion, which amino acids, by themselves or as part of a larger sequence, bind to an antibody generated in response to such sequence.

The term "conformational epitope" shall mean a recombinant epitope having structural features native to the amino acid sequence encoding the epitope within the full length natural protein. Native structural features include, but are not limited to, glycosylation and three dimensional structure. Generally, a conformational epitope is added to the MEFA-containing immunoassay mixture to enhance assay sensitivity and selectivity. Preferably, a recombinant conformational epitope is expressed in a cell from which it is extractable under conditions which preserve its desired structural features, e.g. without denaturation of the epitope. Such cells include bacteria, yeast, insect, and mammalian cells. Preferably, the cell in which a conformational epitope is expressed is a mammalian cell, such as a chinese hamster ovary cell (CHO). Expression and isolation of recombinant conformational epitopes from the E1 and E2 regions of HCV are described in WO 96/04301, WO 94/01778, WO 95/33053, WO 92/08734, which applications are herein incorporated by reference in their entirety.

The term "expression cassette" shall mean a DNA sequence which contains a coding region operably linked to suitable control sequences capable of effecting expression of the coding region in a compatible host. Expression systems invariably comprise a promoter, but, depending on the host intended, may contain additional critical DNA such as ribosome binding site or CAP site, termination sequence, and optional enhancer sequences upstream from the promoter or in other operable locations. The recombinant expression cassettes of the invention herein comprise a DNA of the invention encoding a MEFA operably linked to additional DNA sequences that are capable of effecting its expression. The expression cassette may reside on a transfer vector such as a plasmid or other vector that is self-replicating independently of the chromosome of the host cell, or may be constructed so that when inserted into a host cell it is able to integrate into the chromosome.

The term "equivalent antigenic determinant" shall mean an antigenic determinant from different sub-species or strain of a given organism e.g., a different strain of a virus such as strains 1, 2, and 3 of hepatitis C virus. More specifically for a virus such as hepatitis C, epitopes are known, such as 5-1-1, and such epitopes vary between the known strains 1, 2, and 3. Thus, the epitope 5-1-1 from the three different strains are equivalent antigenic determinants and thus are "copies" even though their sequences are not identical. In general the amino acid sequences of equivalent antigenic determinants will have a high degree of sequence homology, e.g., amino acid sequence homology of more than 30%, preferably more than 40%.

The term "tracer" shall mean any detectable marker molecule attachable to an epitope or a MEFA. Attachment is preferably by covalent means. Detectable marker molecules useful as tracers in the invention include, but are not limited to, dimethyl acridinium ester (DMAE), a chromophore, biotin, strepavidin, an antibody, an antigen, enzymes fluorogenic compounds, rhodamine compounds, fluorescein, FITC, and the like.

Producing Immunoassays-General

Highly sensitive and selective immunoassays can be produced using the multiple epitope fusion antigens of the present invention. In order to produce such immunoassays it is first necessary to identify a target for which a sample is to be assayed, e.g., assay for a particular virus in a body fluid sample. After identifying the virus of interest, the preferred immunodominant epitopes of the virus are isolated, sequenced and nucleotide sequences encoding the amino acid sequences of the epitopes are determined and produced. The nucleotide sequences encoding the amino acid sequences can be fused together using standard recombinant methodology.

The fused sequence must include at least two copies of nucleotide sequences that encode a given epitope. The nucleotide sequence is then placed within an expression cassette and a suitable host is transformed with the cassette. The host is allowed to express the sequences to provide the multiple copy epitopes (multiple epitope fusion antigen, MEFA). The multiple copy epitopes produced are then purified, for example, by affinity chromatography, which process is expedited to a certain degree due to the presence of the multiple copies of a given epitope. The purified MEFAs are then coated onto the surface of the substrate for ELISA-type assays. Alternatively, the purified MEFAs are attached to a detectable marker tracer molecule for detection of antibody binding, such as in a chemiluminescence assay (CLIA).

The essence of the invention is the purified multiple copy epitopes, i.e., purified fusion proteins that include multiple copies of a given epitope fused, in a linear fashion in nature, to other epitopes that are not normally connected to each other in this fashion (MEFAs). The purified epitopes are encompassed by the general structural formula (I) as follows: $(A)_x-(B)_y-(C)_z$, which represents a linear amino acid sequence, B is an amino acid sequence of an epitope or cluster of epitopes and each B contains at least five and not more than 1,000 amino acids, y is an integer of 2 or more, A and C are each independently an amino acid sequence of an epitope or cluster of epitopes not immediately adjacent to B in nature, and x and z are each independently an integer of 0 or more wherein at least one of x and z is 1 or more. When each of x, y, or z is greater than 1 or when each of x, y, and z are greater than 1, the multiple copies of A, B and C may be identical, i.e., each copy of A (different from B and C) is the exact same amino acid sequence, each copy of B (different from A and C) is the exact same amino acid sequence, and each copy of C (different from A and B) is the exact same amino acid sequence. Alternatively, each A, B or C copy may be an equivalent antigenic determinant from different strains of the same virus. Thus, for example, if y is 3, each B may be an identical amino acid sequence or three different sequences from equivalent antigenic determinants from HCV strain 1, 2, and 3. The invention may utilize genetic material encoding known epitopes or groups of epitopes by connecting the material in a nucleic acid construct that produces a multiple copy epitope of the formula (I).

HCV antibody capture assays in which the individual single epitopes are coated on a solid support are less sensitive than capture assays in which a chimeric multiple epitope polyprotein, such as (C25) containing epitopes from the immunodominant core, c33c (NS3), and c1000 (NS4) region sequences (Chien, D. Y., et al (1992) Proc. Natl. Acad. Sci. USA 89:10011–10015, herein incorporated by reference), is coated on a solid support. In turn, a capture assay using the C25 chimeric polyprotein is less sensitive than an HCV antibody capture assay using a MEFA of the invention, which MEFA contains multiple copies of at least one epitope and at least one copy is from a different HCV strain. Thus, a preferred MEFA of the invention having the general formula Ax-By-Cz, contains more than one copy of an epitope (i.e., y is an integer of 2 or more), and at least one of the epitopes of B is a different equivalent antigenic determinant (e.g. an epitope from a different pathogen strain).

The invention disclosed herein utilizes recombinant DNA technology and protein engineering to design a recombinant polyprotein which fuses a variety of different immunodominant epitopes from a variety of pathogens or pathogen strains as the chimeric antigen for immunoassay development. Further, the invention utilizes multiple copies of selected epitopes from structural as well as non-structural coding regions of a gene combined and expressed as a recombinant polyprotein to significantly improve the sensitivity and selectivity of an immunoassay.

Epitopes used in making a multiple copy epitope of the invention can be from a variety of different organisms. For example, the epitope may be an amino acid sequence from bacteria, protozoa, virus, rickettsiae, parasite or fungus. A preferred embodiment of the invention uses epitopes that are extracted from a bacteria or virus, with particularly preferred epitopes being those obtained from a virus, such as from human immunodeficiency virus and, most preferably, from hepatitis C virus.

It is well known that any given organism varies from one individual organism to another and further that a given organism such as a virus can have a number of different strains. For example, hepatitis C virus includes at least strains 1, 2, and 3. Each of these strains will include equivalent antigenic determinants. More specifically, each strain will include a number of antigenic determinants that will be present on all strains of the virus but, will be slightly different from one viral strain to another. For example, hepatitis C includes the antigenic determinant known as 5-1-1 (in the NS3 region of the viral genome). This particular antigenic determinant appears in three different forms on the three different viral strains of hepatitis C. Accordingly, in a preferred embodiment of the invention all three forms of 5-1-1 appear on the multiple epitope fusion antigen of the invention. A MEFA of the invention has the above structural formula I, wherein y is 3 and thus each of the three "Bs" are equivalent antigenic determinants of 5-1-1 taken from the three different viral strains of hepatitis C.

Figure 3:
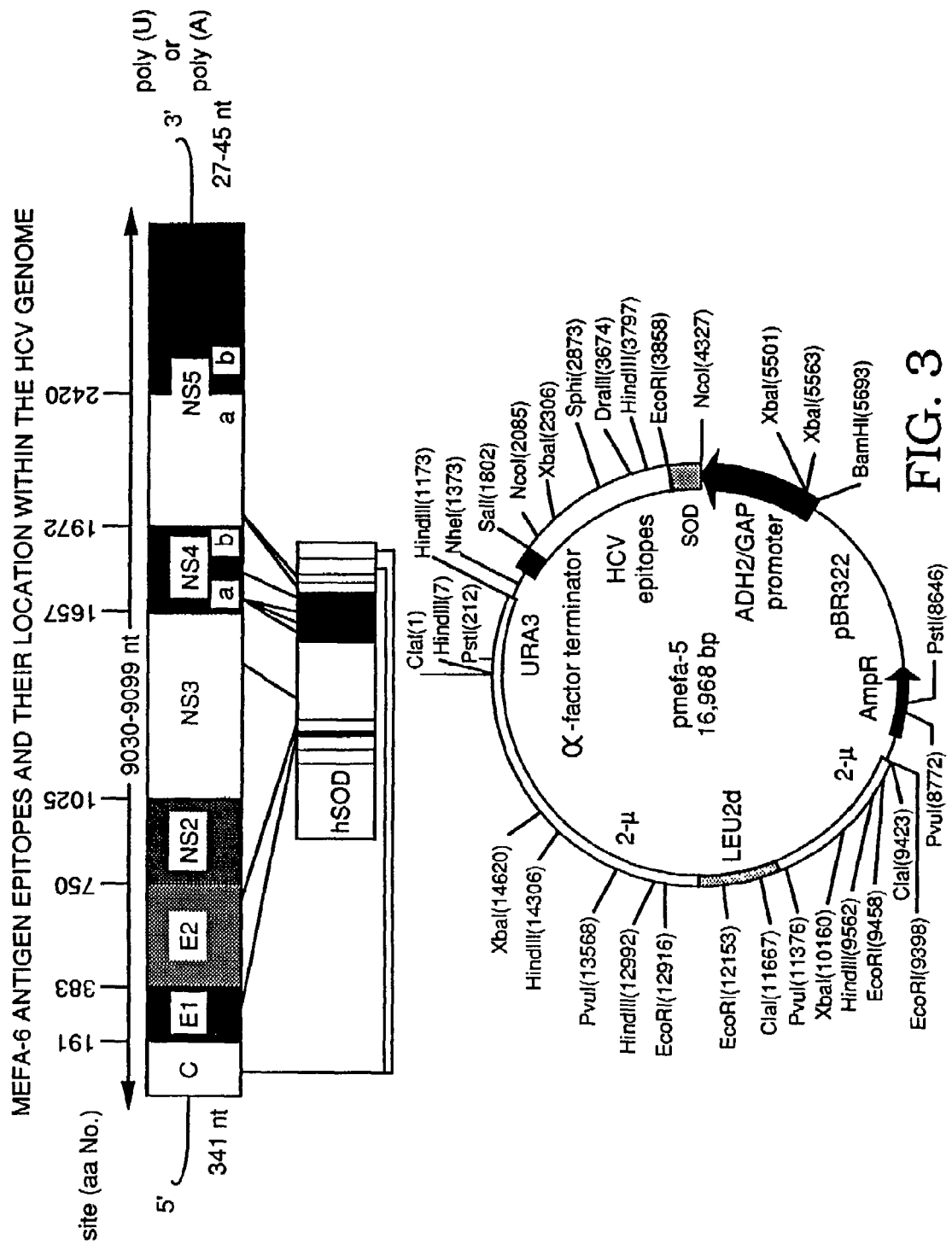
FIG. 3 is a schematic drawing showing the MEFA-6 antigen epitopes and their location within the HCV genome. A diagram of the expression vector for MEFA-6 is also provided.

The multiple copy epitope of the present invention can also include multiple copies which are exact copies of the same epitope. For example, it is desirable to include two copies of an epitope from the core region of hepatitis C. A particularly preferred embodiment of the present invention is the multiple copy epitope as shown within FIG. 3. This multiple copy epitope includes two exact copies of an epitope from the core region and three copies of an epitope from the 5-1-1 region, which copies are equivalent antigenic determinants meaning that they are antigenic determinants taken from the three different viral strains of hepatitis C. In general, equivalent antigenic determinants have a high degree of homology in terms of amino acid sequence which degree of homology is generally 30% or more or more preferably 40% or more.

Producing HCV Immunoassays

Highly selective and sensitive immunoassays generally contain major immunodominant epitopes of the pathogen suspected of infecting a patient. Previously, immunoassays made use of individual epitopes to bind anti-HCV antibodies in biological samples.

For the virus HCV, major immunodominant linear epitopes were identified from the core, NS3 (nonstructural), NS4, and NS5 regions of the virus polyprotein. Sallberg et al. assayed HCV core protein and putative matrix proteins against human serum samples containing antibodies to HCV and defined several immunodominant regions within the HCV proteins (Sallberg, M. et al. (1992) J. Clin. Microbiol. 30:1989–1994). Protein domains of HCV-1 polyproteins including domains C, E1, E2/NS1, NS2, NS3, NS4, and NS5 were identified and their approximate boundaries provided by Chien and Rutter (Chien, D. Y. and Rutter, W., WO 93/00365, international publication date Jan. 7, 1993, herein incorporated by reference in its entirety). Kotwal et al. designed individual polypeptides having sequences derived from the structural region of HCV in order to obtain an immunodominant epitope useful in testing sera of HCV patients (Kotwal, G. J., et al. (1992) Proc. Natl. Acad. Sci. 89:4486–4489).

Serologically definable subtypes of HCV were identified by Chien et al. as viral subtypes exhibiting varied antigenicity (presented at the Third International Hepatitis Meeting, Tokyo, May, 1993 and in Chien, D. Y. et al. (1994) Viral Hepatitis and Liver Disease, pp. 320–324, herein incorporated by reference in its entirety). HCV-1 core, NS4, and NS5 regions were found to contain serotype-specific epitopes. Individual putative core proteins from HCV-1 and HCV-2 were used as individual antigens to produce antibodies for enzyme-linked immunosorbent assays to detect HCV infection using serologically distinguishable core antigen subtypes (Machida, A. et al. (1992) Hepatology 16:886–891). Simmonds et al. investigated the effect of sequence variability between different types of HCV upon the antigenicity of the NS4 protein by epitope mapping and by enzyme-linked immunosorbent assay (ELISA). These authors mapped two major antigenic regions in the HCV NS4 polyprotein that were recognized by antibody elicited upon natural infection by HCV. Type-specific antibody to particular HCV types was also detected (Simmonds, P. et al. (1993) J. Clin. Microbiol. 31:1493–1503). Ching et al. prepared a series of synthetic peptides based on the sequence of a highly conserved region of the HCV putative nucleocapsid (core) protein and found an immunodominant region that was recognized by human and chimpanzee sera (Ching, W.-M. et al. (1992) Proc. Natl. Acad. Sci. 89:3190–3194).

Assays involving single epitopes as test antigens have the disadvantage that it is difficult to control solid phase coating of the support surface by large numbers of individual epitopes containing short peptides. In such cases where the assay involves deposition of an immunogenic antigen on a solid support, the sensitivity of the assay is limited by the amount of antigen that can be coated on the surface of the solid support.

An example of an immunoassay that includes immunodominant epitopes from different regions of a single virus subtype is disclosed within Chien et al. (Proc. Natl. Acad. Sci. USA 89:10011–10015 (1992), herein incorporated by reference). The assay described by Chien utilizes recombinant HCV polypeptides derived from many different regions of the HCV type 1 polyprotein, including that of chimeric recombinant polyprotein, C25, comprises immunodominant components evident in both the structural and non-structural regions. The polyproteins produced are recombinantly derived viral polypeptides and are included on the surface of an immunoassay in order to capture antibodies, i.e., detect the presence of antibodies generated in response to infection with HCV. However, these polyproteins contain epitopes from a single viral strain thereby limiting the ability to detect anti-HCV antibodies from different strains of the virus.

EXAMPLES

The following examples are put forth so as to provide those of ordinary skill in the art with a complete disclosure and description of how to make the multiple copy epitopes and immunoassays of the invention as well as use such and are not intended to limit the scope of what the inventors regard as their invention. Efforts have been made to ensure accuracy with respect to numbers used (e.g. amounts, temperature, etc.) but some experimental error and deviation may be inherent in the description. Unless indicated otherwise, parts or parts by weight, molecular weight is weight average molecular weight, temperature is in degrees Centigrade and pressure is at or near atmospheric.

Example 1

Construction and Expression of an HCV Epitope Polyprotein Expression Cassette

The following example illustrates the concept of preparing a polyprotein cassette of major epitopes, particularly a cassette of multiple epitopes. The example further illustrates the success of using epitopes from different strains of a pathogen. It is also shown that a hydrophilic multiple epitope antigen increases the solubility of the polyprotein. The epitopes are shown to maintain their native local conformation for binding to antibodies as evidenced by the antigenicity of the polyprotein.

The polyprotein expressed from the multiple epitope cassette is referred to herein as a Multiple Epitope Fusion Antigen (MEFA).

Preferably, where an epitope is repeated, the extra copy or copies are tandemly arrayed in the same orientation. It is understood that the region of a viral coding sequence used as an epitope may be varied slightly and still retain antigenic activity, and that the amino acid numbering designation may vary from strain to strain. Thus, the repeated epitopes may vary one from another in amino acid sequence due to strain sequence variations and/or numbering designation. Preferably, the amino acid sequences of repeated epitopes within a MEFA are at least 30% homologous at the amino acid level, more preferably at least 40% homologous at the amino acid level.

Unique restriction enzyme sites were introduced in order to connect the epitopes in the prescribed order and enhance the usefulness of the invention by facilitating modifications in design of a chimeric antigen. The choice of restriction enzyme sites and cloning procedures are readily determined by one of ordinary skill in the art of recombinant DNA technology. Preferably, the epitope junctions (amino acid sequences created between epitopes due to cloning) do not generate non-specific epitopes. Non-specific epitopes are, for example, non-HCV sequences which do not exist adjacent to the HCV epitopes in nature. Non-specific epitopes may bind antibodies in a test sample causing false positive assay results. Preferably, the multiple epitope fusion protein is tested for false positive results due to such sequences generated at the epitope junctions. To avoid non-specific interactions with the MEFA due to junction sequences, the DNA sequence encoding the junction may, for example, be mutated such that (1) non-specific interactions with the mutant amino acid sequence are reduced, and (2) cloning of the epitope fragments is possible.

Construction of a MEFA Expression Cassette of HCV Epitopes

The HCV MEFA-3 expression cassette was constructed by cloning the coding nucleotide sequences containing major epitopes in a tandem array as shown in FIG. 1. A major epitope was chosen based on antibody reaction frequency and reaction intensity (titer) to the epitope (Chein, D. Y. et al. (1994) Viral Hepatitis and Liver Disease, pp. 320–324). The various DNA segments coding for the HCV epitopes were constructed by PCR amplification or by synthetic oligonucleotides. The amino acid codons encoded in each segment are shown below each segment. The complete HCV-1 amino acid sequence (3011 amino acids) was determined by Choo, et al. (1991) PNAS, USA, 88:2451–2455, herein incorporated by reference in its entirety. Oligonucleotides capable of binding to HCV are described in U.S. Pat. No. 5,350,671, herein incorporated by reference in its entirety. The numbering of the amino acids in epitopes of the invention follows the numbering designation provided in Choo, et al., supra, in which amino acid #1 is the first methionine encoded by the coding sequence of core region. For example, an epitope segment from the core region is encoded by amino acid codons 10 to 53 of the HCV core protein. An epitope from the c33c region is encoded by amino acid codons 1192 to 1457. The MEFA-3 construct contains in the expression cassette two copies of the core segment epitope amino acids 10–35; one copy of the c33c epitope segment from amino acids 1192–1457; three copies of equivalent antigenic determinants from the HCV NS4 region, specifically the 5-1-1 region, where two of the epitopes are a segment (amino acids 1694 to 1735) from the NS4 5-1-1 region of HCV type 1, while one copy is segment from the NS4 5-1-1 region of HCV type-2 (Nomoto) from amino acids 1694 to 1735; two copies of the NS4 (C100) C-terminal region major epitopes from amino acids 1901–1940; and two copies of major epitopes from amino acids 2278–2310 of the NS5 region. The MEFA-3 expression cassette has the general structural formula 2-1-2-1-2-2 for Ax-By-Cz, where A=core-core-c33c, x=1; B=(5-1-1), y=3; and C=(c100)-(c100)-(NS5)-(NS5), z=1.

Other HCV MEFAs include MEFA-5 and MEFA-6 for which expression cassettes were constructed by cloning the coding nucleotide sequences containing major epitopes in a tandem array as shown in FIG. 2 and Table 1, and FIG. 3 and Table 2, respectively. It is noted that all of the epitopes in MEFA-5 and MEFA-6 are from HCV type 1 except for two of the three equivalent antigenic determinants of the 5-1-1 epitope. Epitopes from the 5-1-1 region have been found to vary between serotypes of HCV. A copy of each of the HCV type-specific 5-1-1 epitopes present in the MEFAs described herein allows binding of any of the HCV types that may be present in the test biological sample. It is a feature of the invention that an epitope useful in distinguishing serotypes of a virus such as HCV is provided as repeated equivalent antigenic determinants in order to detect multiple types of a virus or pathogen in a single assay. Methods of determining HCV serotype are found in WO 96/27153, herein incorporated by reference in its entirety.

TABLE 1

MEFA-5 Antigen Epitopes and Their Location Within the HCV Genome

| mefa aa# | 5' End Site | Epitope | HCV aa# | Strain |
|---|---|---|---|---|
| 1–154 | NcoI | hSOD | | |
| 159–202 | EcoRI | core | 10–53 | 1 |
| 205–246 | SacI | core | 10–53 | 1 |
| 251–268 | PstI | E1 | 303–320 | 1 |
| 271–309 | HindIII | E2 | 405–444 | 1 |
| 310–576 | DraIII | c33c | 1192–1457 | 1 |
| 579–625 | SphI | 5-1-1 | 1689–1735 | 1 |
| 628–674 | NruI | 5-1-1 | 1689–1735 | 3 |
| 677–723 | ClaI | 5-1-1 | 1689–1735 | 2 |
| 726–765 | AvaI | c100 | 1901–1940 | 1 |
| 768–803 | XbaI | NS5 | 2278–2313 | 1 |
| 806–841 | Bg/II | NS5 | 2278–2313 | 1 |

TABLE 2

MEFA-6 Antigen Epitopes and Their Location Within the HCV Genome

| mefa aa# | 5' End Site | Epitope | HCV aa# | Strain |
|---|---|---|---|---|
| 1–154 | NcoI | hSOD | | |
| 159–176 | EcoRI | E1 | 303–320 | 1 |
| 179–217 | HindIII | E2 | 405–444 | 1 |
| 218–484 | DraIII | c33c | 1192–1457 | 1 |
| 487–533 | SphI | 5-1-1 | 1689–1735 | 1 |
| 536–582 | NruI | 5-1-1 | 1689–1735 | 3 |
| 585–631 | ClaI | 5-1-1 | 1689–1735 | 2 |
| 634–673 | AvaI | c100 | 1901–1940 | 1 |
| 676–711 | XbaI | NS5 | 2278–2313 | 1 |
| 714–749 | Bg/II | NS5 | 2278–2313 | 1 |
| 750–793 | NcoI | core | 10–53 | 1 |
| 796–839 | SacI | core | 10–53 | 1 |

The cloning procedures for preparation of MEFA-5 and MEFA-6 were similar to those used for preparing MEFA-3, above. MEFA-5 and MEFA-6 contained epitopes from the core, envelope, NS3, NS4 and NS5 regions of the hepatitis C polyprotein, including equivalent antigenic determinants from HCV strains 1, 2, and 3. The various DNA segments coding for the HCV epitopes were constructed by PCR amplification or by synthetic oligonucleotides. FIGS. 2 and 3 are diagrammatic representations showing the location of epitopes within the HCV genome used in MEFA-5 and -6, as well as the MEFA vector construction. Tables 1 and 2 describe the amino acid segments of each epitope, the linear arrangement of the various epitopes and the number of copies in the MEFA-5 and MEFA-6 cassettes, respectively. The amino acids between each epitope (junction amino acids) are derived from the restriction sites used for cloning. Preferably, a MEFA is tested in an immunoassay for a false positive result due to the non-pathogen (HCV, for example) junction amino acids. MEFA-5 differs from MEFA-6 in linear arrangement in that the core segments are near the N-terminus in MEFA-5, but are at the C-terminus in MEFA-6. As the amino acid 10–53 core epitope is highly antigenic, its placement at the C-terminus improves the antigenicity of the MEFA possibly by improved interaction of epitopes from core proteins and antigens from me E1 and E2 regions with the anti-HCV antibodies of the sample.

The epitopes were subcloned into a yeast expression vector and the sequences verified before assembling the entire fusion antigen as an EcoRI-SalI fragment of 2060 bp (for MEFA-5 and MEFA-6) and as an EcoRI-SalI fragment of approximately 1927 bp (for MEFA-3). MEFA-5 and MEFA-6 were cloned as SOD fusion proteins (157 amino acids of human superoxide dismutase (hSOD)) under the regulation of the hybrid $ADH_2$-GAPDH promoter. The MEFA-5 and MEFA-6 expression cassettes were ligated to the yeast shuttle vector pAB24 (Chiron Corporation) to produce pMEFA-5 and MEFA-6, as shown in FIG. 2 and FIG. 3, respectively.

As shown in FIG. 3, the MEFA-6 antigen includes multiple copies of HCV epitopes from the core and NS5 region; different serotype epitopes from the NS4 5-1-1 region; a single copy of major linear epitopes from the c100 C-terminal regions, E1, and E2 regions, as well as the HCV NS3 (c33c) region. The general structural formula for MEFA-6 is hSOD-E1-E2-c33c-5-1-l(type 1)-5-1-1(type 3)-5-1-1(type 2)-c100-NS5(2 copies)-core(2 copies). This antigen has a very high expression level in yeast, purifies to a high degree of homogeneity, and exhibits high sensitivity and high selectivity in the immunoassays described below.

Expression of a MEFA in Yeast The following example of the expression of a MEFA in yeast may be applied to the expression of any MEFA of the invention. It is within the scope of the instant invention to vary the conditions, as necessary, to express a particular MEFA construct. Cells preferred for expression of a MEFA of the invention include bacteria, yeast, and insect cells. The expression of MEFA-6 in yeast is provided as a non-limiting example of the instant invention.

Yeast strains AB122, JSC310, and AD2 (Chiron Corporation) were transformed with the appropriate MEFA expression plasmid (such as pMEFA-6) using a lithium acetate protocol. Ura⁻ transformants were streaked for single colonies and patched onto Leu⁻/8% glucose plates to increase plasmid copy number. Leu⁻ starter cultures were grown for 24 hours at 30° C. and then diluted 1:20 in YEPD (yeast extract bactopeptone glucose) media. The cells were grown for 48 hours at 30° C. and harvested. To test for expression of the MEFA-6 recombinant antigen, an aliquot of the cells (0.5 OD unit equivalent) was boiled in SDS (sodium dodecylsulfate) gel electrophoresis sample buffer (e.g. Lammli buffer) containing 50 mM DTT and the protein components of the cell mixture were separated by gel electrophoresis on an Tris-glycine polyacrylamide gel. MEFA-6 was highly enriched in the insoluble pellet fraction.

Purification of a MEFA Protein in Yeast

The following procedure describes the purification of a specific MEFA, MEFA-6. The techniques and conditions are not intended to limit the invention, as one of ordinary skill in the art may find it necessary to adjust conditions for the purification of another MEFA of the invention. Unless otherwise indicated, purification of a MEFA is conducted at approximately 0° C.

MEFA-6 was expressed in *S. cerevisiae* and cells were harvested as described above. The cells were suspended in lysis buffer (50 mM Tris, 0.15 M NaCl, 1 mM EDTA, 1 mM PMSF, pH 8.0) and lysed in a Dyno-Mill (Wab Willy A. Bachofon, Basel, Switzerland) or equivalent apparatus using glass beads. The lysate was centrifuged at low speed conditions (3,000 to 5,000 rpm, 15 min) and the pellet containing the insoluble protein fraction was washed with increasing concentrations of urea (1 M, 2 M, 3 M) in lysis buffer. Protein was solubilized from the centrifugation pellet with 0.1 N NaOH, 4 M urea in lysis buffer. Cell debris was removed by low speed centrifugation at 3,000 to 5,000 rpm, 15 min. The supernatant was adjusted to pH 8.0 with 6 N HCl to precipitate proteins insoluble under these conditions.

The precipitate was removed by centrifugation and the supernatant was adjusted to 2.3% SDS, 50 mM DTT, pH 8.0 and boiled for 3 min. Proteins in the mixture were fractionated by gel filtration on a Pharmacia Sephacryl S-400 in phosphate buffered saline containing 0.1% SDS, 1 mM EDTA and adjusted to pH 7.4. Column eluate fractions containing MEFA-6 were collected, pooled, and concentrated on an Amicon YM-30 membrane. Gel filtration was repeated on the pooled fractions using the same column and conditions.

Evaluation of the Antigenicity of a MEFA

In order to evaluate the antigenicity of a chimeric antigen of the invention, the epitopes of MEFA-3 were exposed to polyclonal or monoclonal antibodies raised to specific individual epitopes. Purified recombinant multiple epitope fusion antigens (MEFA) were diluted to optimal coating concentration in phosphate-buffered saline (pH 7.4) and coated on Immulon I plates (Dynatech). Monoclonal antibodies to core, NS3 (c33c), NS4 (c100 and 5-1-1), NS5 and polyclonal antisera anti-E1 and E2 from rabbits were prepared by standard techniques (BIOS-Chile, Maraton 1943, Santiago, Chile) and were diluted 200-fold in sample diluent on the plate and incubated for 1 hr at 37° C., and washed with plate wash buffer (PBS, 0.075% Tween-20, pH 7.2). Either goat anti-mouse F(ab')$_2$ or affinity purified goat anti-rabbit IgG heavy and light chain specific antibody conjugated to horseradish peroxidase (diluted 1:5000 for anti-mouse conjugate; diluted 1:10,000 for anti-rabbit conjugate) were added to each assay well. The plates were incubated for 1 hr at 37° C. and washed. o-Phenylenediamine dihydrochloride (OPD) and hydrogen peroxide were added for horse radish peroxidase (HRPO) reaction color development. The optical density readings were determined using a plate reader at 492/620 nm.

The results indicated that all of the antigen epitopes within the designed MEFA were easily detected by the specific HCV antibodies for all of the MEFAs of the invention. For example, Table 3 provides data on the immunoreactivity of the individual epitopes, as well as the chimeric antigen, MEFA-3, to monoclonal antibodies of HCV-specific epitopes. As shown in Table 3, core, c33c, c100, 5-1-1, and NS5 epitopes of MEFA-3 were immunoreactive with HCV-specific antibodies. Table 4 shows that the epitopes c33c, c22, 5-1-1, c100, NS5, E1, and E2 of MEFA-5 and MEFA-6 were immunoreactive with HCV-specific antibodies.

TABLE 3

HCV Specific Epitopes of MEFA-3 Antigen:
Evaluation by Anti-HCV Monoclonal Antibodies

| HCV Mab ID# | 3G1-1 | 4D1-1 | 22AFG3 | 20AGF3 | 5A1/F5 | Comment Results |
|---|---|---|---|---|---|---|
| Mab Specificity | anti-core | anti-c33c | anti-5-1-1 | anti-c100 | anti-ns-5 | |
| Recombinant Test antigens | OD | OD | OD | OD | OD | |
| SOD (non-recombinant) | 0.001 | 0.001 | 0.002 | 0.002 | 0.003 | No reaction with SOD |
| C25 | 2.755(+) | 2.813(+) | 2.726(+) | 0.028(−) | 0.023(−) | React with epitopes of core, c33c & 5-1-1 |
| c22 (core) | 2.700(+) | 0.043(−) | 0.035(−) | 0.036(−) | 0.038(−) | React with epitope of core |
| c33c (NS3) | 0.029(−) | 2.646(+) | 0.018(−) | 0.020(−) | 0.014(−) | React with epitope of c33c |
| c100 (NS4) | 0.020(−) | 0.022(−) | 2.907(+) | 3.021(+) | 0.016(−) | React with epitopes of 5-1-1 and C-terminal epitope of c100 |

TABLE 3-continued

HCV Specific Epitopes of MEFA-3 Antigen: Evaluation by Anti-HCV Monoclonal Antibodies

| HCV Mab ID# | 3G1-1 | 4D1-1 | 22AFG3 | 20AGF3 | 5A1/F5 | Comment Results |
|---|---|---|---|---|---|---|
| NS5 | 0.012(−) | 0.029(−) | 0.009(−) | 0.009(−) | 2.513(+) | React with epitope of NS5 |
| Test Antigen MEFA-3 | 3.236(+) | 3.236(+) | 3.467(+) | 0.713(+) | 0.024(−) | React with epitopes of core c33c, 5-1-1 and c100 |

TABLE 4

HCV Epitope Exposure Within MEFA-5 and MEFA-6

| Antibody ID | Antibody Specifity | Antigenic to HCV sequence region | MEFA-6 epitope exposure OD | MEFA-5 epitope exposure OD |
|---|---|---|---|---|
| Mab 3G1-1 | anti-core (c22c) | (aa# 10–50) | 3.018 (R) | 2.702 (R) |
| Mab 4D1-1 | anti-NS3 (c33c) | linear epitope of c33c | 3.119 (R) | 2.952 (R) |
| Mab 6C10/D1 | anti-NS4 (c100) | (aa# 1901–1940) | 3.853 (R) | 2.998 (R) |
| Mab 22A5/C12 | anti-NS4 (5-1-1) | (aa# 1689–1735) | 3.006 (R) | 3.192 (R) |
| Mab 3E1/F1 | anti-NS5 | (aa# 2297–2313) | 2.808 (R) | 2.863 (R) |
| Mab 1E5/F10 | anti-NS5 | (aa# 2297–2313) | 2.892 (R) | 2.784 (R) |
| polyclonal R667 | anti-E1 | (aa# 192–380) | 4.375 (R) | 1.908 (R) |
| polyclonal R669 | anti-E2 | (aa# 404–662) | 1.76 (R) | 0.963 (R) |
| Cutoff value | | | 0.45 OD | 0.45 OD |

R = Reaction
NR = No Reaction

Figure 4:
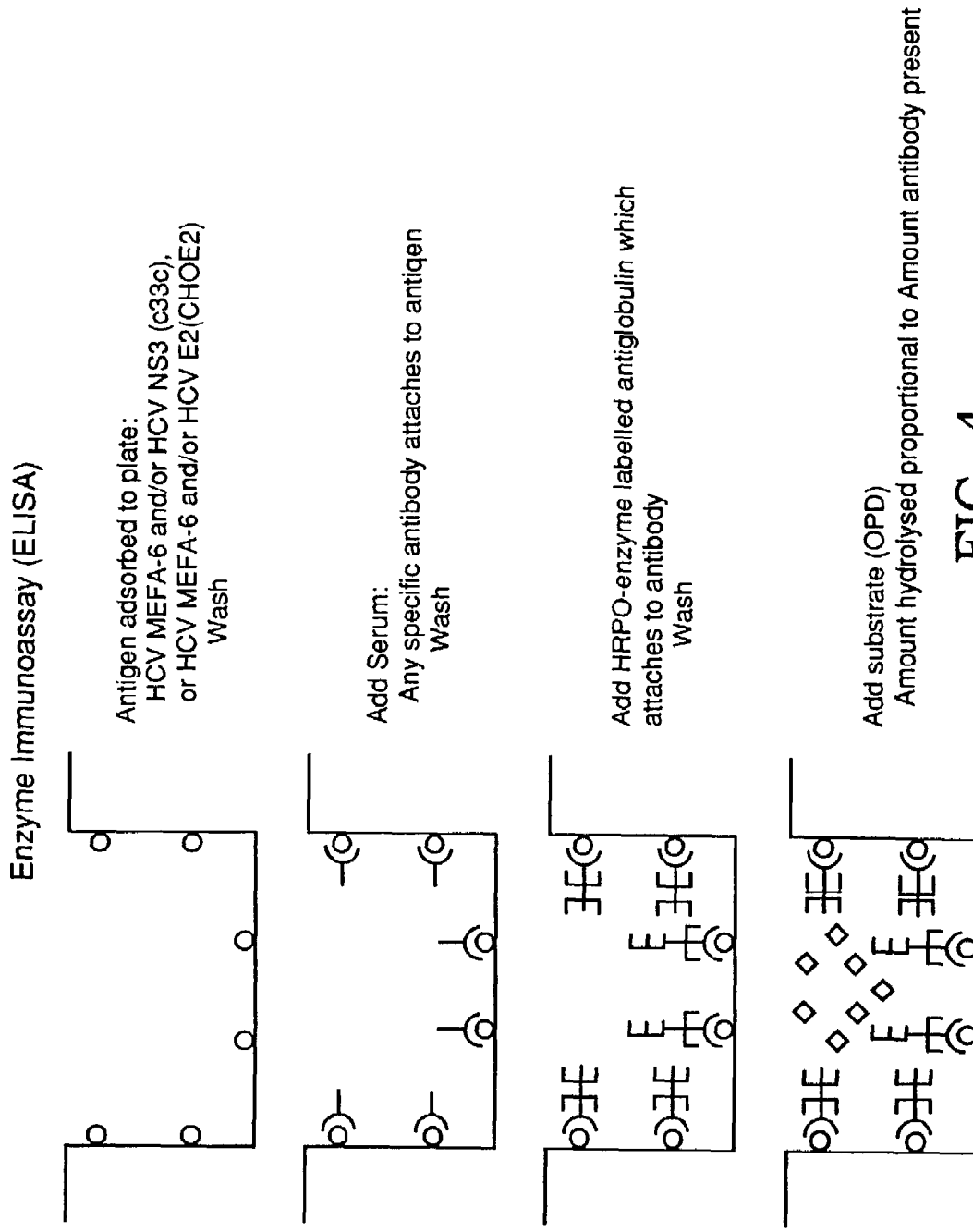
FIG. 4 is a schematic drawing of an enzyme-linked immunosorption assay (ELISA) in which a MEFA is adsorbed onto the surface of a solid support.

Inhibition Assays: Peptide inhibition assays were performed to test whether serotype specific epitopes on a MEFA antigen detect HCV type-specific antibodies in serum. The assay evaluated the degree to which a MEPA in solution would bind to serum HCV type-specific antibodies, thereby inhibiting the subsequent ELISA reaction in which the serotype-specific peptides are the antigenic species on a solid support. FIG. 4 is a schematic drawing of a standard ELISA procedure in which binding to the solid support-bound antigen is detected by enzyme catalyzed hydrolysis.

Inhibition assays were performed by multi-antigen ELISA. Recombinant HCV antigens were prepared as described in Chien et al. (1992) PNAS 89:10011–10015. The c22 (119 amino acids), E1 (130 aa), NS5 (942 aa), and chimeric C25 (858 aa) antigens were expressed as internal antigens within the yeast S. cerevisiae as C-terminal fusions with human superoxide dismutase (SOD) using methods described previously for the generation of the c100-3 (363 aa) antigen (Kuo, G. et al. (1989) Science 244:362–364, herein incorporated by reference; and Cousens, L. S. et al. (1987) Gene 61:265–275, herein incorporated by reference). The c33c antigen (363 amino acids) was expressed as an internal SOD fusion polypeptide in E. coli by methods described for the synthesis of the 5-1-1 antigen (Choo, O.-L. et al. (1989) Science 244:359–362, herein incorporated by reference). The recombinant HCV antigens were purified as described in Chien, D. Y. et al. ((1989) PNAS 89:10011–10015, supra), herein incorporated by reference).

Prior to performing the inhibition assays, the patient sample dilution breaking points were determined (Table 5). Patient samples were serially diluted and tested for reaction to recombinant c22, c33c, c100 and NS-5 antigens immobilized separately onto a solid support (see, for example, Van der Poel, C. L. et al. (1991) Lancet 337:317–319, herein incorporated by reference). The dilution breaking point was the greatest dilution at which binding was still detectable. For optimal detection in subsequent inhibition assays, the patient samples were less dilute than the dilution breaking point dilution, as indicated in Table 6.

TABLE 5

Detection Limit Determination for Patient Samples MEFA-3 Antigen Epitopes

| HCV Patient Sample ID | Sample Dilution Breaking Points Recombinant Antigens | | | |
|---|---|---|---|---|
| | c22 | c33c | c100 | NS5 |
| PAA LL57366 | 1:8 | 1:128 | neat | neat |
| PAA LL57454 | 1:32 | 1:128 | 1:8 | neat |
| PAA FF25946 | 1:32 | 1:256 | 1:32 | NR |
| PAA FF25912 | ND | ND | ND | neat |

NR = no reaction
ND = not done

In general, the inhibition assays were performed by the following procedure. Recombinant HCV antigens and denatured SOD (control) were diluted to optimal concentration in phosphate-buffered saline (pH 7.4) and coated on Immulon I plates (Dynatech). A 200 μl aliquot of either 30% fetal calf serum (FCS) or MEFA-3 peptide (5 or 10 μg per assay as indicated) dissolved in 30% FCS was mixed on the plate with 5 μl of diluted serum or plasma specimen. The samples were incubated for 1 hr at 37° C. and washed with plate wash buffer. Polyclonal goat anti-human IgG (heavy- and light-chain-specific) antibody conjugated to either $^{125}$I or horseradish peroxidase (HRP) was added to each well. The plates were incubated for 1 hr at 37° C. and then washed. o-Phenylenediamine dihydrochloride and hydrogen peroxide were added for HRP color development. The results were read using a plate reader at 492 nm/620 nm (ELISA). The ELISA cutoff OD values for antigens from regions SOD, C25, c22, E1, E2, c33c, and NS-5 were 0.40 plus the mean OD of three negative control sera included in each assay. If the control SOD antigen was reactive, then that sample was considered to be nonreactive or indeterminate. The percentage of binding inhibition was calculated by the following formula: 100×(A492 nm for patient sample without added MEFA antigen)−(A492 nm for patient sample with added MEFA antigen)/(A492 nm for patient sample without added MEFA antigen). The % inhibition of binding to type specific peptides caused by added MEFA-3 indicates that the ability of the epitopes within MEFA-3 to bind the anti-HCV antibodies of the patient samples (See Table 6).

The ability of MEFA-3 to interact with anti-HCV type 1 and anti-HCV type 2 antibodies was demonstrated by inhibition studies using a MEFA ELISA protocol. Individual synthetic peptides from HCV type 1a, 1b, 2a, and 2b 5-1-1 regions were immobilized on separate solid supports. The ability of the synthetic peptides from the 5-1-1 region to bind the type specific patient antibodies was determined by competition with added MEFA-3. The results in Table 7 show that MEFA-3 inhibits binding of HCV 1a, 1b, 2a, and 2b to the individual type specific epitopes (amino acids 1689–1718 from the 5-1-1 region). The ability of a MEFA to bind antibodies to two different strains of HCV was the same for MEFA-3, MEFA-5, and MEFA-6.

TABLE 7

HCV Type Specificity: MEFA-3 5-1-1 Epitopes Interact With Antibodies to HCV Types 1 and 2

| | Control HCV Type Specific Peptides | | | | Inhibition, % HCV Type Specific Peptide + MEFA-3 | | | |
|---|---|---|---|---|---|---|---|---|
| | HCV1a (1689–1718) epitope | HCV1b (1689–1718) epitope | HCV2a (1689–1718) epitope | HCV2b (1689–1718) epitope | | | | |
| Sample | specific ELISA OD | specific ELISA OD | specific ELISA OD | specific ELISA OD | HCV1a ELISA OD | HCV1b ELISA OD | HCV2a ELISA OD | HCV2b ELISA OD |
| (A) HCV-Type 1 Sample | | | | | | | | |
| #4(1:10d) | 1.093 | 0.073 | 0.002 | 0.004 | 0.165 | 0.136 | 0.044 | 0.014 |
| % Inhibition | | | | | 85% | 0% | 0% | 0% |
| (B) HCV-type 1b sample | | | | | | | | |
| #358 | 0.964 | 1.543 | 0.424 | 0.235 | 0.438 | 0.261 | 0.284 | 0.234 |
| % Inhibition | | | | | 55% | 83% | 33% | 0% |
| (C) HCV-type 2 sample | | | | | | | | |
| #32(1:10d) | 0.001 | 0.001 | 0.839 | 0.460 | 0.007 | 0.018 | 0.034 | 0.055 |
| % Inhibition | | | | | 0% | 0% | 96% | 88% |

TABLE 6

Binding Inhibition by Specific Epitopes of MEFA-3

| Patient Sample | | Control | MEFA-3 Added | |
|---|---|---|---|---|
| ID | Dilution | OD | OD | % Inhibition |
| c22 Antigen | | | | |
| LL57366 | 1:4 | 1.614 | 0.163 | 90% |
| LL57454 | 1:16 | 1.370 | 0.212 | 84.5% |
| FF25946 | 1:16 | 2.013 | 0.205 | 90% |
| c33c Antigen | | | | |
| LL57366 | 1:64 | 2.525 | 0.07 | 99% |
| LL57454 | 1:64 | 1.839 | 0.075 | 96% |
| FF25946 | 1:128 | 0.842 | 0.061 | 93% |
| c100 Antigen | | | | |
| LL57454 | 1:4 | 1.666 | 0.484 | 71% |
| FF25946 | 1:16 | 2.364 | 0.092 | 96% |
| NS-5 Antigen | | | | |
| LL57454 | Neat | 2.319 | 1.820 | 20% |
| FF25912 | Neat | 1.490 | 0.873 | 41% |

Example 2

Sensitivity of ELISA Using a MEFA as the Antigen

A comparison of dilution sensitivity was made between MEFA ELISA (MEFA-3) and C25 ELISA. HCV polyprotein C-25 (c33c-c100-3-c22) and assay procedures were as described by Chien, D. Y. et al. (1992) PNAS USA 89:10011–10015, supra) using a coating buffer of 1×phosphate buffered saline (PBS), pH 7.0–7.2. Antigens were coated onto the surface of Immulon I plate microliter wells at 100 ng antigen per well plus 5 μg/ml BSA. Sample size was 5 μl per assay. The goat anti-human IgG (heavy- and light-chain-specific) antibody conjugated to horse radish peroxidase was diluted 1:60,000 for the MEFA-3 assay, and 1:40,000 for the C25 assay. The results in Table 8 show that serum antibodies are detectable using MEFA-3 ELISA at dilutions at which the C25 ELISA showed no reaction. The sensitivity of MEFA-3, -5, and -6 CLIA were compared to each other and to C25 ELISA. The results in Table 9 show that MEFA-5 and MEFA-6 CLIA provided superior sensitivity to MEFA-3 CLIA, while MEFA-3 CLIA was more sensitive than C25 ELISA.

TABLE 8

Dilution Sensitivity:
Comparison Study between MEFA ELISA and C-25 ELISA

| Sample Panel ID | | MEFA-3 ELISA<br>Immulon I plate<br>100 ng/well + 5 ug/ml BSA<br>Conjugate: 1:60000<br>Sample size: 5 ul/assay<br>OD | C-25 ELISA<br>Immulon I plate<br>100 ng/well + 5 ug/ml BSA<br>Conjugate: 1:40000<br>Sample size: 5 ul/assay<br>OD |
|---|---|---|---|
| Sample | Dilution | | |
| LL57454 | | | |
| | 1:512 | 0.983 | 0.734 |
| | 1:1024 | 0.652 | NR |
| | 1:2048 | 0.463 | NR |
| LL57366 | | | |
| | 1:512 | 0.609 | 0.425(+/−) |
| | 1:1024 | 0.522(+/−) | NR |
| | 1:2048 | 0.203 | NR |
| FF25946 | | | |
| | 1:100 | 1.818 | 1.736 |
| | 1:1000 | 0.763 | 0.525 |
| | 1:2000 | 0.718 | NR |
| | 1:4000 | 0.455 | NR |
| Seroconversion Panel C | Bleed Date | | |
| C7 (8/29/88) | day 1 | 0.562 | NR |
| C8 (9/01/88) | day 4 | 1.035 | 0.667 |
| C9 (9/28/88) | day 32 | 2.762 | 2.145 |
| Men of negative sample OD | | 0.124 | 0.086 |
| Cutoff OD | | 0.55 | 0.45 |

(+/−) = OD near cutoff value
NR = Non-reactive
C-25 ELISA is equivalent to 2G (Second Generation) HCV ELISA

TABLE 9

Dilution Sensitivity of MEFA-3 vs. −5 vs. −6 vs. c25
SENSITIVITY PANEL

| Patient Sample | | MEFA-3 CLIA S/C.O. | MEFA-5 CLIA S/C.O. | MEFA-6 CLIA S/C.O. | c25 ELISA S/C.O. |
|---|---|---|---|---|---|
| FF25946 | 1:16 | 1.71 | 2.72 | 2.67 | 1.32 |
| | 1:32 | 1.64 | 2.59 | 2.48 | 1.35 |
| | 1:64 | 1.50 | 1.89 | 2.11 | 1.20 |
| | 1:128 | 1.34 | 1.92 | 1.68 | 0.92 |
| | 1:256 | 1.11 | 1.48 | 1.68 | 0.91 |
| | 1:512 | 0.84 | 1.14 | 1.28 | 0.69 |
| | 1:1024 | 0.58 | 0.82 | 1.11 | 0.63 |
| LL57385 | 1:16 | 1.73 | 2.74 | 2.68 | 1.49 |
| | 1:32 | 1.56 | 2.41 | 2.18 | 1.04 |
| | 1:64 | 1.20 | 1.76 | 1.79 | 1.00 |
| | 1:128 | 0.87 | 1.10 | 1.03 | 0.61 |
| | 1:256 | 0.76 | 0.93 | 0.90 | 0.57 |
| | 1:512 | 0.51 | 0.68 | 0.64 | 0.48 |
| | 1:1024 | 0.38 | 0.47 | 0.45 | 0.39 |
| | 1:2048 | 0.23 | 0.33 | 0.29 | 0.20 |
| FF25879 | 1:16 | 1.70 | 2.79 | 2.54 | 1.46 |
| | 1:32 | 1.66 | 2.73 | 2.38 | 1.03 |
| | 1:64 | 1.30 | 1.82 | 1.88 | 0.86 |
| | 1:128 | 1.21 | 1.35 | 1.17 | 0.73 |
| | 1:256 | 0.96 | 1.20 | 1.14 | 0.66 |
| | 1:512 | 0.60 | 0.88 | 0.73 | 0.52 |
| | 1:1024 | 0.48 | 0.76 | 0.36 | 0.50 |
| | 1:2048 | 0.42 | 0.65 | 0.44 | 0.40 |
| LL57366 | 1:16 | 1.67 | 2.71 | 2.59 | 1.59 |
| | 1:32 | 1:32 | 2.30 | 1.92 | 1.15 |
| | 1:64 | 1.11 | 1.65 | 1.57 | 0.96 |
| | 1:128 | 1.19 | 1.35 | 1.09 | 0.77 |
| | 1:256 | 0.84 | 1.02 | 1.11 | 0.63 |
| | 1:512 | 0.55 | 0.83 | 0.88 | 0.50 |
| | 1:1024 | 0.55 | 0.60 | 0.54 | 0.47 |
| | 1:2048 | 0.38 | 0.49 | 0.58 | 0.37 |

TABLE 9-continued

Dilution Sensitivity of MEFA-3 vs. -5 vs. -6 vs. c25
SENSITIVITY PANEL

| Patient Sample | | MEFA-3 CLIA S/C.O. | MEFA-5 CLIA S/C.O. | MEFA-6 CLIA S/C.O. | c25 ELISA S/C.O. |
|---|---|---|---|---|---|
| LL57454 | 1:16 | 1.87 | 3.10 | 2.59 | 1.80 |
| | 1:32 | 1.57 | 2.82 | 2.16 | 1.33 |
| | 1:64 | 1.30 | 2.17 | 1.38 | 1.14 |
| | 1:128 | 1.11 | 1.66 | 1.38 | 0.79 |
| | 1:256 | 0.63 | 1.07 | 1.04 | 0.60 |
| | 1:512 | 0.51 | 0.76 | 0.74 | 0.43 |
| | 1:1024 | 0.41 | 0.52 | 0.54 | 0.34 |
| | 1:2048 | 0.22 | 0.45 | 056 | 0.30 |

S/CO = sensitivity (OD)/cutoff (OD)

A seroconversion sensitivity assay measures the sensitivity of the method to detecting pathogen-specific antibodies as the titers increase in response to infection. The sensitivity of MEFA-3 ELISA compared to C25 ELISA for blood samples from a single HCV-infected patient over time is provided in Table 8. MEFA-3 detected antibodies with greater sensitivity at an earlier time post-infection that the C25 ELISA.

Sensitivity and Convenience of a Chemiluminescence Immunoassay Using MEFA Relative to an Existing Commercial Assay MEFA as Tracer.

MEFA-6 recombinant antigen was used to design a manual chemiluminescence immunoassay (CLIA) as well as an automated CLIA on the Ciba Corning ACS-NG system (F-model).

Figure 5:
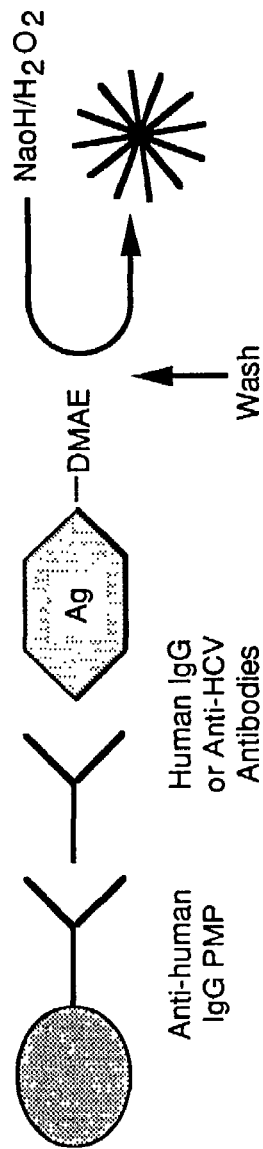
FIG. 5 is a schematic diagram of an antibody capture format for detection of anti-HCV antibodies by chemiluminescence in which a MEFA is attached to a detectable marker molecule, DMAE. Also indicated is a format in which a MEFA (MEFA-6) and an additional epitope (c33c) are the antigens of the assay.

A CLIA, designated the HCV r-Ag-DMAE CLIA (HCV recombinant antigen-dimethyl acridinium ester chemiluminescence immunoassay) was developed (FIG. 5). A polypeptide or synthetic peptide antigen was labeled with DMAE by reaction of amino acid side chains (e.g. lysine e side chain or cysteine thiol) with a reactive moiety covalently linked to DMAE (see WO 9527702, published Oct. 19, 1995, Ciba Corning Diagnostics Corp., herein incorporated by reference). The HCV MEFAs described herein were labeled by reaction with the amino groups of lysine side chains with NSP-DMAE-NHS (2',6'-Dimethyl-4'-(N-succinimidyloxycarbonyl)phenyl 10-(3'-Sulfopropyl)-acridinium-9-carboxylate) obtained from Ciba Corning. Thiols of amino acid side chains can be labeled using DMAE-ED-MCC or NSP-DMAE-PEG-BrAc (Ciba Corning). Labeling procedures were generally as described in WO 9527702 (supra) with variations in conditions as necessary for each antigen to provide optimal detection and antigenicity. It is understood that other detectable markers are useful in the invention, such as fluorescent compounds, rhodamine compounds, antibodies, antigens, enzymes, and the like. Labeling with any marker is carried out under conditions for obtaining optimal detection and antigenicity of the of MEFA or other epitope.

Where DMAE is the detectable marker in an assay, the resultant HCV r-Ag-DMAE conjugate is the tracer, with DMAE detectable by light emission when reacted with NaOH/$H_2O_2$. When a particular MEFA, such as MEFA-6, was used in the assay, it was designated the MEFA-6-DMAE CLIA.

Manual assay. A manual HCV r-Ag-DMAE CLIA protocol used for the studies disclosed herein is first described. A Magic Lite Analyzer System II (MLA II) was used for the manual assay. Parameters such as volume, concentration, time, and temperature are provided for guidance. Variation of these parameters to obtain antibody detection is within the scope of the invention. A 2–10 μl aliquot of test sample was added to corresponding tubes. The test sample was preferably a biological fluid (plasma or serum, for example) containing anti-HCV antibodies. To each tube was added 50 μl of water followed by 100 μl biotinylated recombinant antigens, synthetic peptides, or directly conjugate DMAE to the polypeptides (MEFA-6-DMAE, c33c-DMAE, c200-DMAE, and c22-DMAE, for example). The antigens were diluted in ligand reagent (LR) diluent to concentrations from approximately 0.1 μg/assay to 1 μg/assay. Preferably, an amount of ligand reagent was added to each sample such that approximately 25×10$^6$ light unit equivalents (relative light units, RLU) were present per assay. This approximate amount of light unit equivalents was preferred for the addition of a single ligand, or for multiple ligands. LR diluent contained Tris buffer, pH 8.0, 150 mM NaCl, 1.0% BSA, 0.1% Tween-20, 0.09% NaN$_3$, 1 mM EDTA. A 150 μl aliquot of PMP (paramagnetic particles) attached to anti-human IgG Fc was added to each tube for a final concentration of 60 μg/assay. Preferably, the paramagnetic particles were less than approximately 10 μm in diameter. The anti-IgGFc-PMP particles were diluted in a diluent containing Tris buffer, pH 8.0, 150 mM NaCl, 2.75% BSA, 0.1% casein, 0.1% Tween-20, 0.1% yeast extract, 0.25% E. coli extract, 0.005% SOD, 0.09% NaN$_3$, 1 mM EDTA. To ensure complete mixing, the tubes were shaken on a Vortex mixer 6 times at 5–10 seconds each time. The sample tubes were incubated at 37° C. for 18 minutes. The sample tubes were placed on a magnet for 3 minutes, for sufficient time to sediment the PMP particles. The samples were decanted using a magnet to retain the PMP particles. The PMP particles were washed twice with vortexing in 1 ml of PBS. The wash solution was PBS, 0.1% Tween-20, 0.09% NaN$_3$, 1 mM EDTA. The steps of mixing, incubating, sedimenting and decanting may be repeated at least one time. To each tube 100 μl of water was added to resuspend the PMP particles. The tubes were then placed in an MLA-II instrument and light emission was measured for 2 seconds.

The manual MEFA-6-DMAE CLIA method provided enhanced detection sensitivity relative to the MEFA-6 ELISA. Following the study of eight dilution sensitivity panels, it was found that the MEFA-6-DMAE CLIA demonstrated a better dilution sensitivity than ELISA in six out of eight panels.

Importantly, the MEFA-6-DMAE CLIA method detected the presence of HCV antibodies in all samples from chronically infected HCV patients tested. For example, of 29 chronic hepatitis C infected individuals, 26 tested positive using a C25 ELISA, while all 29 tested positive using the MEFA-6-DMAE CLIA of the invention. In addition, no false positive results were found during the testing of 200 random samples by MEFA-6-DMAE CLIA. Other advantages of the CLIA method are inter-assay and intra-assay precision with covariences of less than 10%. In addition, the CLIA had a wider response range and improved linearity relative to ELISA.

Automated Assay. An automated MEFA-DMAE assay having the following protocol was also used. An F model automated analyzer was used for the assay. A 10 µl sample (such as a biological fluid containing human anti-HCV antibodies) was added to each sample tube. The automated sampler then simultaneously dispensed into each sample tube the following: 100 µl of HCV r-Ag-DMAE conjugate (having a total of approximately $25 \times 10^6$ light unit equivalents per test) plus 150 µl anti-human IgGFc attached to paramagnetic particles (60 µg IgGFc per assay) plus a 40 µl water backing. The ligand diluent and the IgG-PMP diluent were as described above for the manual assay. No mixing by vortex was required. The samples were heated to 37° C. for 18 min on a heating block. The anti-human IgG FC PMP particles which bound to the HCV antibodies present in the serum sample were washed three times with resuspension in a wash buffer of PBS containing 0.1% Tween 20, 0.09% $NaN_3$, 1 mM EDTA. A magnet was used to retain the PMP particles while the sample supernatants were aspirated. The particles were resuspended in 500 µl wash buffer. Using the automated method, it was not necessary to repeat the mixing, incubating, sedimenting, and decanting steps thereby making the HCV r-Ag-DMAE CLIA assay both efficient (20 minutes versus 40 minutes), sensitive, and accurate relative to existing commercial assays.

Figure 7:
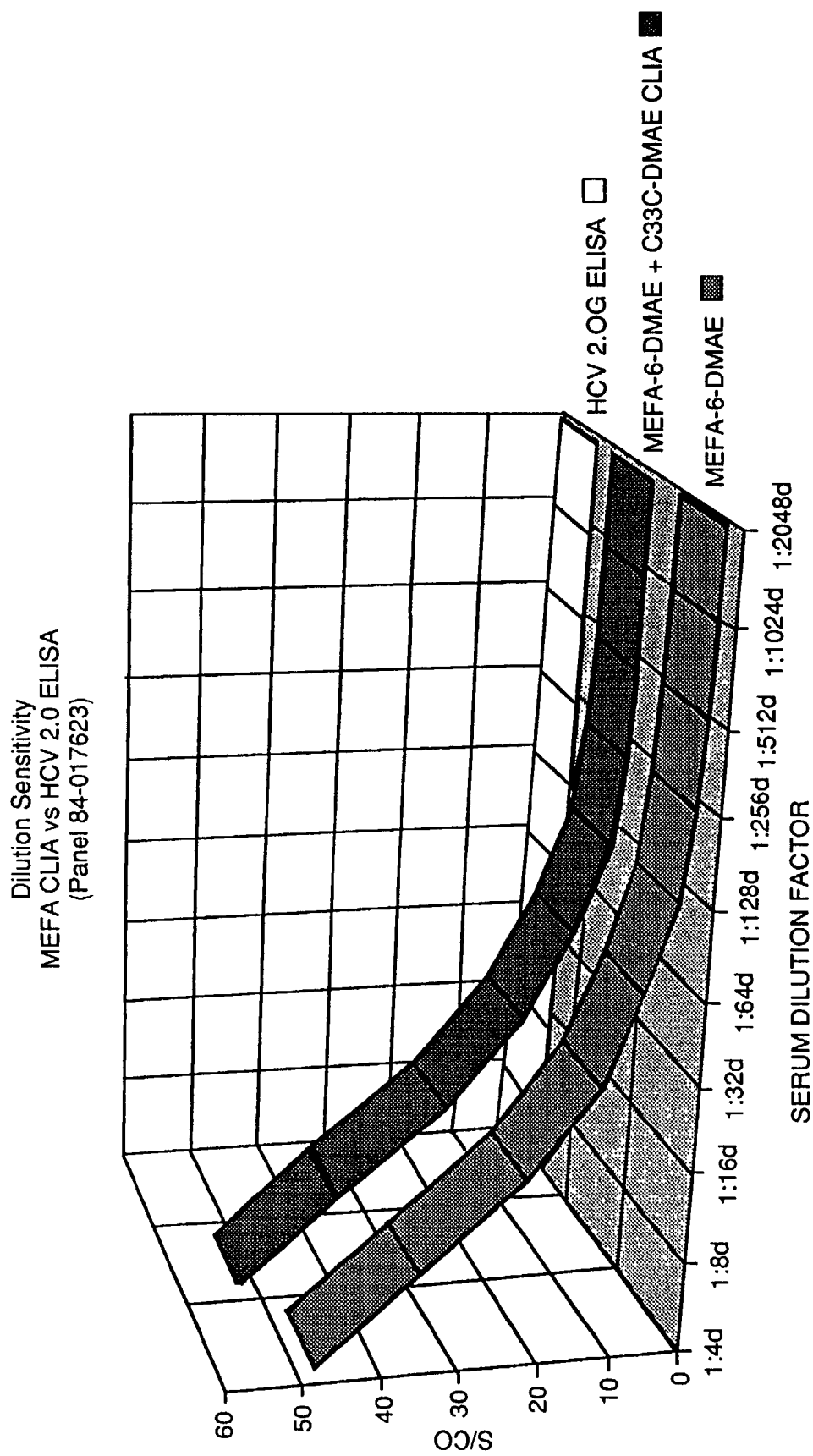
FIG. 7 is a plot comparing the dilution sensitivity of MEFA-6-DMAE and MEFA-6-DMAE +c33c-DMAE to the dilution sensitivity of a commercial ELISA, HCV 2.0G (second generation) ELISA.

The MEFA-6-DMAE CLIA and the MEFA-6-DMAE +c33c-DMAE CLIA had better or equivalent sensitivities and specificities when compared to the multiantigen HCV 2.0G ELISA tests (Chiron Corp., Emeryville, Calif.), which contain the separate recombinant peptides c100-3, c22-3, and c200 (c33c linked to c100-3) (see FIG. 7). Further, the assay method of the invention is easy to perform because it is a one-step simultaneous assay on a single instrument using one convenient, recombinant capture antigen. According to further embodiments of the invention the additional epitope may a different epitope of the MEFA, such as conformational epitopes CHO E1 or CHO E2 (HCV epitopes E1 or E2 expressed from chinese hamster ovary cells) and labeled with a detectable marker as described for additional epitope c33c in the above example. Such conformational epitopes from HCV and immunoassays involving them are described in WO 96/04301, WO 94/01778, WO 95/33053, WO 92/08734, supra.

Seroconversion Sensitivity

The seroconversion sensitivity of the MEFA-6 chimeric antigen was also determined by CLIA (DMAE as detectable marker) and compared to commercial ELISA methods. In addition to using the MEFA-6-DMAE alone as an antigen, a mixture of MEFA-6-DMAE +c33c-DMAE was tested for seroconversion sensitivity as another embodiment of the invention. Blood samples were obtained from a chronically infected HCV patient over time, tested by CLIA using the procedure described above, and compared with the performance of Ortho 3.0 EIA (ELISA) (Table 10, only) and Abbott 2.0 ELISA (see FIG. 8 and Table 10). Sensitivity was reported as the optical density of the assay sample divided by the assay detection cut off in optical density units (S/CO).

The detection of HCV antibody in these samples was also performed by a commercial strip immunoblot assay (RIBA® 3.0 Chiron Corporation), which assay is used clinically as a confirmatory test for HCV antibody detection. According to the RIBA® method, recombinant HCV antigens are separated by gel electrophoresis and contacted with patient serum. Reactivity with the separated antigens is performed by immunoblot assay using secondary labeled antibodies (Eheling, F. et al. (1991) Lancet 337:912–913).

Figure 8:
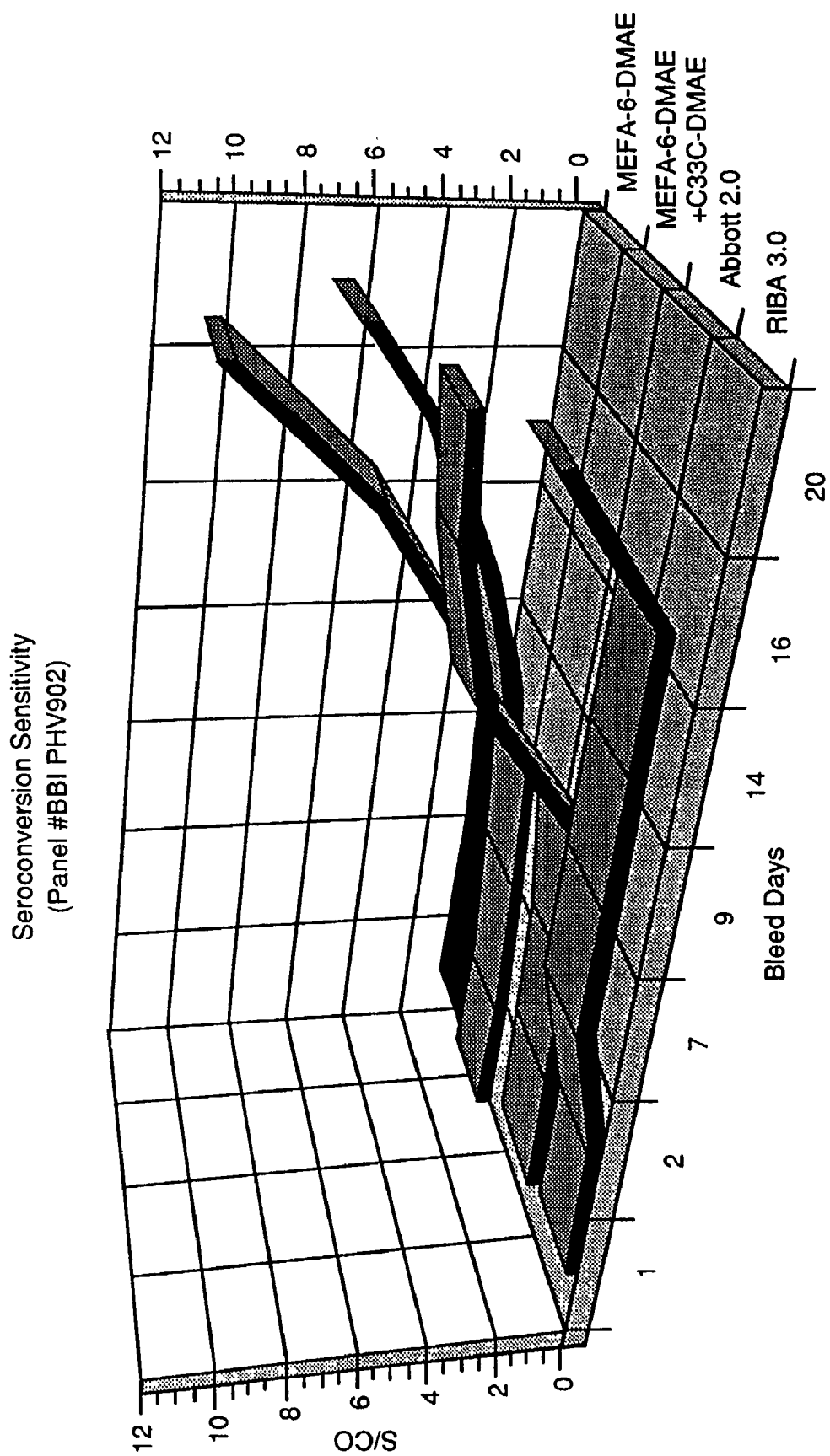
FIG. 8 is a plot comparing the seroconversion sensitivity of a commercial ELISA (Abbott Laboratories), MEFA-6, MEFA-6+c33c, and RIBA® 3.0. Samples were taken from a chronically infected patient over time (bleed dates).

The results of the comparison in FIG. 8 and Table 10 indicate that the MEFA-6-DMAE+c33c-DMAE assay was able to detect HCV antibodies with greater sensitivity at an earlier bleed date. The MEFA-6-DMAE and MEFA-6-DMAE+c33c-DMAE assays were more sensitive at earlier bleed times than either the commercial assays or the confirmatory RIBA® test.

Figure 9:
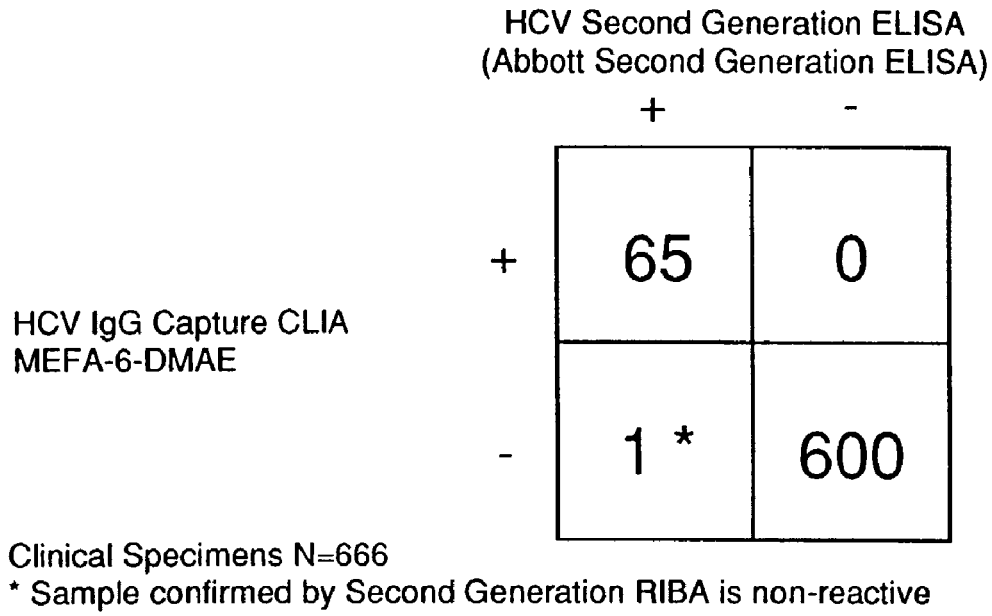
FIG. 9 is a diagram correlating HCV antibody detection (positive or negative) in samples by HCV Second Generation ELISA to detection by MEFA CLIA.
Figure 9:
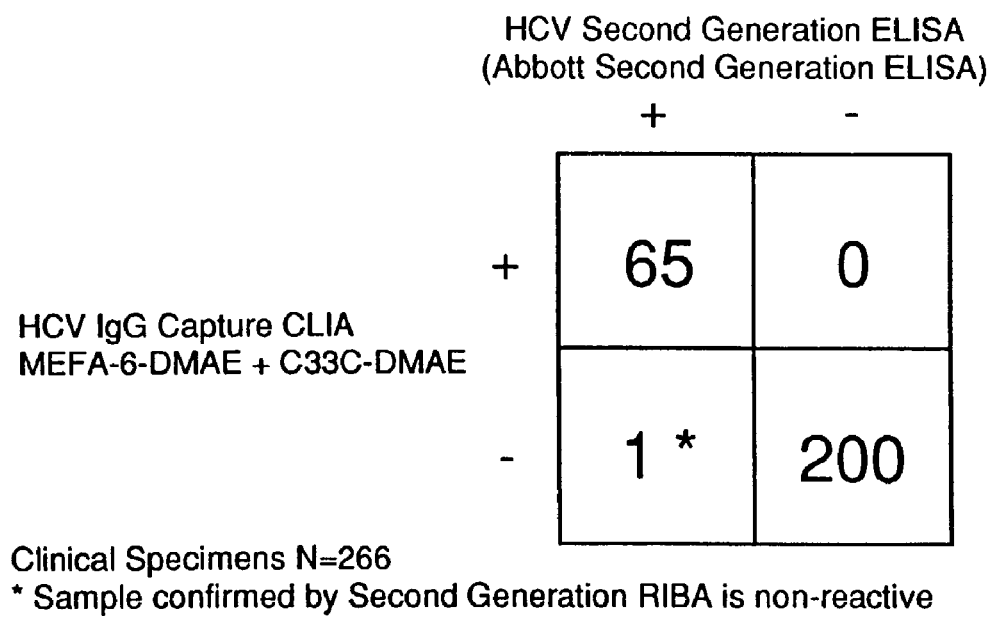

The MEFA CLIA method of the invention was compared to ELISAs from commercial sources to confirm that the MEFA CLIA reliably detects true positive and true negative samples. The results in FIG. 9 show that the HCV antibody detection using MEFA CLIAs of the invention is consistently correlated with the antibody detection of the HCV Second Generation ELISA used commercially (Abbott Laboratories). In the cases where a sample was assayed as positive for HCV antibodies by the commercial assay and negative by the MEFA CLIA, the sample was found to be negative (non-reactive) by the confirmatory $RIBA^{3.0}$ test, further supporting the accuracy of the MEFA CLIA of the invention.

TABLE 10

Seroconversion Sensitivity

| Patient Bleed Day | MEFA-6 CLIA | MEFA 6 + c33c CLIA | Ortho 3.0 ELISA | Abbott 2.0 ELISA | RIBA* 3.0 |
|---|---|---|---|---|---|
| 1 | 0.63 | 0.93 | 0.02 | 0.2 | 0 (Nonreactive) |
| 2 | 0.63 | 0.94 | 0.02 | 0.2 | 0 (Nonreactive) |
| 7 | 0.63 | 1.17 | 1.45 | 0.4 | I (Intermediate) |
| 9 | 0.74 | 1.27 | 2.74 | 0.8 | I (Intermediate) |
| 14 | 1.99 | 3.54 | 4.11 | 3.9 | I (Intermediate) |
| 16 | 3.64 | 6.38 | 4.11 | 5 | I (Intermediate) |
| 20 | 6.84 | 10.9 | 4.11 | 5.3 | 4 (Reactive) |

Seroconversion panel ID: Boston Biomedical, Inc. anti-HCV Serconversion panel (PHV902)

Figure 10:
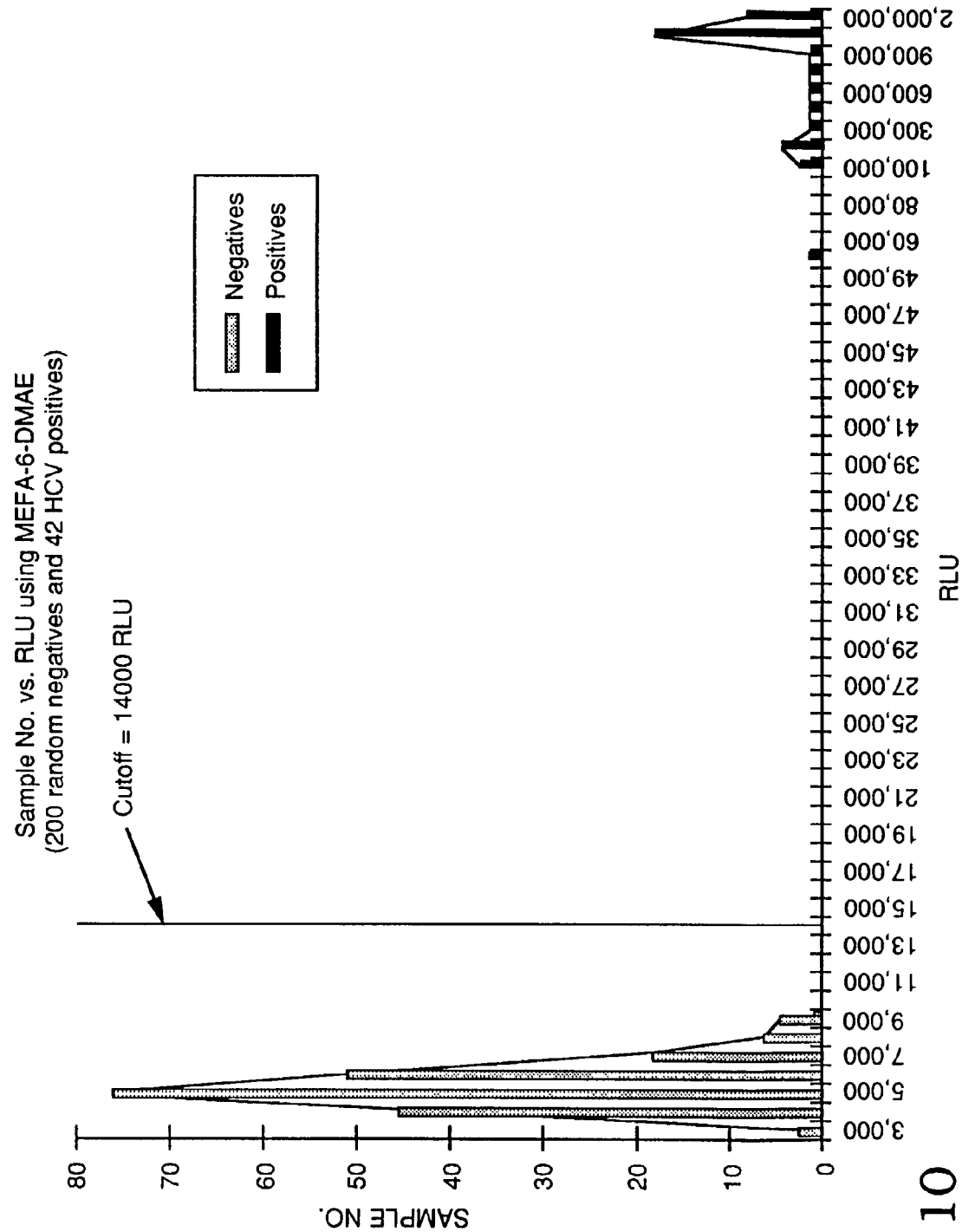
FIG. 10 is a chart illustrating the accuracy of the MEFA-6-DMAE chemiluminescence immunoassay (CLIA) of the invention. All known negative samples exhibited relative light units (RLU) below the cutoff value, while known positive samples exhibited RLUs well above the cutoff value.

The accuracy of detection of HCV antibodies was further demonstrated using MEFA-6-DMAE CLIA (see FIG. 10). Two hundred random negative samples from blood donation centers and 42 known HCV positive samples were tested using the MEPA-DMAE CLIA protocol described above. As FIG. 10 indicates, no false positives were found when testing the negative samples, and no negative results were obtained when testing the known positive samples.

Biotinylated MEFA.

A chemiluminescence immunoassay (CLIA) was developed in which a MEFA was attached to biotin as a detectable marker and indirectly attached to DMAE via a biotin-strepavidin-DMAE link. According to this method, anti-human IgGFc-PMP particles as described above were contacted with a biological fluid containing human anti-HCV antibodies. The human antibodies were bound to the anti-human IgGFc-PMP particles and the MEFA-biotin was bound to the human anti-HCV antibodies. Strepavidin-DMAE conjugate was then bound to the MEFA-biotin. Approximately $25 \times 10^6$ light unit equivalents of the strepavidin-DMAE were added to each test sample. Unbound material was washed from the sample and the light emitted by the reaction of the PMP particle bound DMAE with NaOH/H$_2$O$_2$ was measured for 2 seconds.

Figure 6:
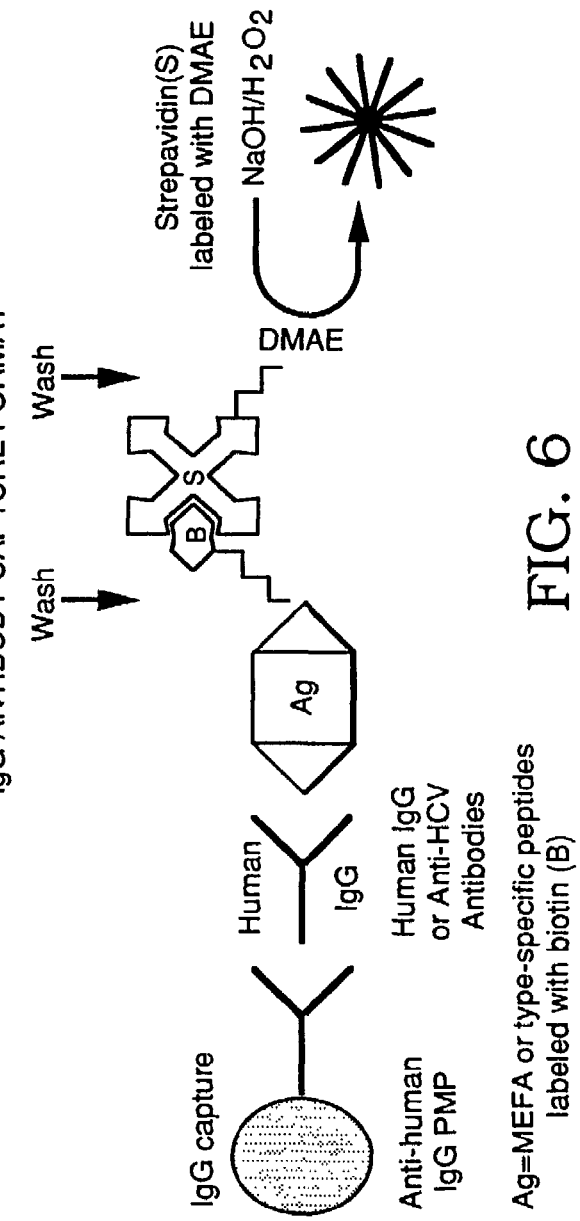
FIG. 6 is a schematic diagram of an antibody capture format for detection by chemiluminescence of human anti-pathogen antibodies in which an antigen (MEFA) is attached to biotin (B) that binds strepavidin labeled with DMAE.

This MEFA CLIA method differs from the MEFA-DMAE CLIA also described herein in that the latter has the DMAE tracer molecule attached directly to the MEFA, whereas the biotinylated MEFA CLIA involves an additional biotin/strepavidin link to bind the DMAE tracer molecule to the anti-HCV/MEFA complex. A diagrammatic representation of the assay procedure is provided in FIG. 6.

The CLIA in which a MEFA is attached to biotin can be automated as described for the MEFA-DMAE CLIA described above. Under these circumstances, strepavidin-DMAE would be added to the sample for binding and detection. Approximately 25×10$^6$ light unit equivalents of the strepavidin-DMAE conjugate are preferably added to the test mixture.

The instant invention has been shown and described herein and was considered to be the most practical, and preferred embodiments. It is recognized, however, that departures may be made therefrom which are within the scope of the invention, and that obvious modifications will occur to one skilled in the art upon reading this disclosure.

What is claimed is:

1. A method for detecting antibodies to hepatitis C virus (HCV) in a biological sample suspected of containing antibodies, the method comprising the steps of
    contacting said sample with a multiple copy epitope sequence comprising the general structural formula (I):

$(A)_x$–$(B)_y$–$(C)_z$  (I)

wherein (I) is a linear amino acid sequence;
    (B) is an amino acid sequence containing at least five and not more than 1,000 amino acids which amino acids correspond to a naturally occurring antigenic determinant of a hepatitis C virus (HCV) polyprotein;
    (A) and (C) are each amino acid sequences different from (B) and different from each other and are each independently an amino acid sequence containing at least five and not more than 1,000 amino acids which amino acids represent an antigenic determinant that is not adjacent to (B) in naturally-occurring strains of HCV;
    x is an integer of 2 or more and at least two (A)s are the same antigenic determinant from the same HCV strain;
    y is an integer of 2 or more and at least two (B)s are the same or an equivalent antigenic determinant from different HCV strains; and wherein (A), (B) and (C) are in any linear order; under conditions that permit antibody-antigen reaction; and
    detecting the presence of immune complexes of said antibodies and said antigens.

2. The method of claim 1, wherein (A), (B), and (C) are epitopes from a single organism.

3. The method of claim 1, wherein (A), (B), and (C) are epitopes from 2 organisms.

4. The method of claim 1, wherein y is 2 or more and at least one (B) is an equivalent antigenic determinant from a different strain of said organism.

5. The method of claim 1, wherein copies of any one or more of (A), (B), and (C) are identical amino acid sequences when any one or more of x, y and z are greater than 1.

6. The method of claim 1, wherein (A), (B), and (C) are in a linear order that is different from the linear order of the naturally occurring antigenic determinants.

7. The method of claim 1, wherein y is 3 and wherein one (B) is an equivalent antigenic determinant from a hepatitis C strain selected from the group consisting of HCV-1, HCV-2, and HCV-3.

8. The method of claim 1, wherein (A), (B), and (C) are epitopes of a hepatitis C virus, wherein y is 3 and wherein each (B) is an equivalent antigenic determinant from HCV-1, HCV-2, and HCV-3.

9. The method of claim 8, wherein x is 2 and each (A) is an epitope from the core region of the HCV polyprotein.

10. The method of claim 8, wherein each (B) is an epitope from the 5-1-1 region of the HCV polyprotein and x is 2, and each (A) is an epitope from the core region of the HCV polyprotein.

11. The method of claim 8, wherein (B) is an epitope from the 5-1-1 region of the HCV polyprotein and z is 2, and each (C) is an epitope from the core region of the HCV polyprotein.

12. The method of claim 1, wherein (B) is from the NS3 region of an HCV polyprotein.

13. The method of claim 1, wherein z is not zero.

14. The method of claim 1, wherein any of (A), (B), and (C) are separated by one or more amino acids.

15. The method of claim 14, wherein (A), (B), and (C) are separated by one or more amino acid sequences containing at least five and not more than 1,000 amino acids, which amino acids correspond to an antigenic determinant, and wherein (A), (B), and (C) are not positioned relative to each other in this manner in nature.

16. The method of claim 1, wherein (A), (B), and (C), are epitopes from regions of the HCV polyprotein, wherein said regions are selected from the group consisting of NS3, NS4, NS5, c100, C25, core, E1, E2, c33c, c100-3, and c22.

17. The method of claim 1, wherein the multiple epitope polypeptide comprises the formula of the MEFA-3 antigen as depicted in FIG. 1.

18. The method of claim 1, wherein the multiple epitope polypeptide comprises the formula of the MEFA-5 antigen as depicted in FIG. 1.

19. The method of claim 1, wherein the multiple epitope polypeptide comprises the formula of the MEFA-6 antigen as depicted in FIG. 1.

20. The method of claim 1, further comprising the step of coating the multiple epitope polypeptide on a surface of a solid matrix.

21. The method of claim 20, wherein the solid matrix is selected from the group consisting of the surface of a microtiter plate well, a bead and a dipstick.

22. The method of claim 1, further comprising the step of attaching a detectable marker to the multiple epitope polypeptide.

23. The method of claim 22, wherein the detectable marker is selected from the group consisting of a chromophore, an antibody, an antigen, an enzyme, an enzyme reactive compound whose cleavage produce is detectable, biotin, streptavidin, a fluorescent compound, a chemiluminescent compound and combinations thereof.

24. The method of claim 1, wherein said antibody-antigen complexes are detected by incubating the complexes with a labeled anti-human immunoglobulin antibody.

25. The method of claim 24, wherein said anti-human immunoglobulin is enzyme labeled.

26. The method of claim 1, wherein said biological sample is selected from human blood, serum or plasma.

27. The method of claim wherein 1, said multiple epitope polypeptide is prepared by chemical synthesis.

28. The method of claim 1, wherein said multiple epitope polypeptide is prepared by recombinant DNA expression.

* * * * *